United States Patent
Boyd et al.

(10) Patent No.: US 9,975,066 B2
(45) Date of Patent: May 22, 2018

(54) AUTOMATED LAYER BY LAYER CONSTRUCTION OF MULTILAYER COATED CORES BY TFF

(71) Applicant: Artificial Cell Technologies, Inc., New Haven, CT (US)

(72) Inventors: James Gorham Boyd, Madison, CT (US); Naveen Palath, Cheshire, CT (US); Edwin Jonathan Cardenas, Waterford, CT (US)

(73) Assignee: ARTIFICIAL CELL TECHNOLOGIES, INC., New Haven, CT (US)

( * ) Notice: Subject to any disclaimer, the term of this patent is extended or adjusted under 35 U.S.C. 154(b) by 284 days.

(21) Appl. No.: 14/719,363

(22) Filed: May 22, 2015

(65) Prior Publication Data

US 2015/0343332 A1    Dec. 3, 2015

Related U.S. Application Data

(60) Provisional application No. 62/003,242, filed on May 27, 2014.

(51) Int. Cl.
*A61F 2/07*        (2013.01)
*A61K 9/50*        (2006.01)
(Continued)

(52) U.S. Cl.
CPC .......... *B01D 21/262* (2013.01); *A61K 9/5031* (2013.01); *A61K 39/00* (2013.01);
(Continued)

(58) Field of Classification Search
CPC .. B01D 21/262; B01D 2221/10; B01D 61/20; B01D 61/22; B01D 2311/06; B01D 2311/12; B01D 2311/16; B01D 2311/25; B01D 2311/2653; B01D 2313/16; B01D 2313/18; B01D 2315/10; A61K 9/5031; A61K 39/00; A61K 9/50; A61K 9/5005; A61K 9/5052; B05D 1/007; A61F 2/07; A61F 2310/0038; A61F 2310/00976; B05C 11/10; B05C 11/1002; B05C 11/1005;
(Continued)

(56) References Cited

U.S. PATENT DOCUMENTS 5,560,902 A    10/1996    Cacheris et al.
6,713,533 B1 *  3/2004    Panzner .................. A61K 9/127
                                                424/450
(Continued)

FOREIGN PATENT DOCUMENTS

WO     2011043360 A1    4/2011

OTHER PUBLICATIONS

Hirsjarvi et al.; "Layer-by-Layer Surface Modification of Lipid Nanocapsules"; European Journal of Pharmaceutics and Biopharmaceutics; 76; pp. 200-207; (2010).
Njegic-Dzakula et al.; "Calcite Crystal Growth Kinetics in the Presence of Charged Synthetic Polypeptides"; Crystal Growth & Design; 9(5); pp. 2425-2434; (2009).
Njegic-Dzakula et al.; "Effects of Initial Supersaturation on Spontaneous Precipitation of Calcium Carbonate in the Presence of Charged Poly-L-amino Acids"; Journal of Colloid and Interface Science; 343; pp. 553-563; (2010).
(Continued)

*Primary Examiner* — Joseph Drodge
(74) *Attorney, Agent, or Firm* — Cantor Colburn LLP

(57) ABSTRACT

Layer by layer ("LBL") construction of products by tangential flow filtration (TFF), or the like, is described, including computer controlled automation of such procedure for production of a multilayer coated core.

27 Claims, 18 Drawing Sheets

(51) Int. Cl.
*A61K 39/00* (2006.01)
*B01D 61/20* (2006.01)
*B01D 61/22* (2006.01)
*B05C 11/10* (2006.01)
*B05C 19/06* (2006.01)
*B05D 1/00* (2006.01)
*B01D 21/26* (2006.01)

(52) U.S. Cl.
CPC ............. *B01D 61/20* (2013.01); *B01D 61/22* (2013.01); *B05C 11/10* (2013.01); *B05C 19/06* (2013.01); *B05D 1/007* (2013.01); *B01D 2221/10* (2013.01)

(58) Field of Classification Search
CPC ............. B05C 11/1007; B05C 11/1026; B05C 11/1036; B05C 11/1039; B05C 19/06
USPC ....... 118/429, 621, 663, 679, 683, 684, 696, 118/699, 702, 712, 602, 603, 610; 210/101, 134, 138, 139, 143, 194, 195.2, 210/198.1, 205, 257.2, 321.6, 639, 650, 210/805; 424/490, 491, 499; 623/1.44, 623/1.46, 1.48
See application file for complete search history.

(56) References Cited

U.S. PATENT DOCUMENTS

| | | | |
|---|---|---|---|
| 6,896,926 B2* | 5/2005 | Qiu | A61L 27/34 427/2.1 |
| 6,923,865 B2 | 8/2005 | Serafin et al. | |
| 7,615,530 B2 | 11/2009 | Haynie | |
| 2002/0092809 A1* | 7/2002 | Ries | B01D 67/0004 210/500.27 |
| 2002/0136776 A1 | 9/2002 | Fang et al. | |
| 2005/0084536 A1 | 4/2005 | Van Buitenen et al. | |
| 2007/0129792 A1* | 6/2007 | Picart | C08J 3/246 623/1.46 |
| 2008/0017576 A1* | 1/2008 | Belfort | B01D 61/142 210/641 |
| 2008/0243113 A1* | 10/2008 | Shastri | A61L 27/047 606/33 |
| 2008/0269468 A1* | 10/2008 | Vogel | B01D 61/145 530/414 |
| 2009/0047517 A1* | 2/2009 | Caruso | B01J 13/14 428/402.24 |
| 2010/0028553 A1* | 2/2010 | Maly | B05D 1/007 427/462 |
| 2012/0009254 A1 | 1/2012 | Powell et al. | |
| 2012/0156256 A1* | 6/2012 | Bonnet-Gonnet | A61K 9/0019 424/400 |
| 2012/0196990 A1 | 8/2012 | Ramstack et al. | |
| 2013/0259946 A1 | 10/2013 | Powell et al. | |
| 2013/0260419 A1* | 10/2013 | Ransohoff | C12M 47/10 435/69.6 |
| 2013/0280797 A1* | 10/2013 | Rao | C12M 47/12 435/288.7 |
| 2014/0026714 A1 | 1/2014 | Murphy et al. | |
| 2015/0057319 A1* | 2/2015 | Kalofonos | A61K 31/427 514/369 |
| 2017/0090490 A1* | 3/2017 | Mills | G05D 21/02 |

OTHER PUBLICATIONS

Voigt et al.; "Membrane Filtration for Microencapsulation and Microcapsules Fabrication by Layer-by-Layer Polyelectrolyte Adsorption"; Ind. Eng. Chem. Res.; 38; pp. 4037-4043; (1999).

Volodkin et al.; "One-Step Formulation of Protein Microparticles with Tailored Properties: Hard Templating at Soft Conditions"; Advanced Functional Materials; DOI:10.1002/adfm.201102007; 9 pages; (2012).

International Search Report and Written Opinion; International Application No. PCT/US15/32108; International Filing Date May 22, 2015; File Reference ATE0035PCT; dated Aug. 12, 2015; 19 pages.

* cited by examiner

AUTOMATED LAYER BY LAYER CONSTRUCTION OF MULTILAYER COATED CORES BY TFF

CROSS-REFERENCE TO RELATED APPLICATIONS

This application claims priority to U.S. Provisional Application No. 62/003,242 filed on My 27, 2014, which is incorporated herein by reference in its entirety.

STATEMENT REGARDING FEDERALLY SPONSORED RESEARCH & DEVELOPMENT

This invention was made with government support under AI091089 awarded by the National Institutes of Health. The government has certain rights in the invention.

TECHNICAL FIELD

This disclosure relates to layer by layer ("LBL") fabrication of products by tangential flow filtration (TFF), or the like. In particular, the present disclosure relates to automation of such procedure, itself, and as it relates to scalability of manufacture of product, which in exemplary embodiments, includes microparticulate constructs such as microparticulate vaccines.

BACKGROUND

Generally, the layer by layer technique is one in which substrates including particles are coated with layers, such as alternating layers of polyelectrolytes. As described in U.S. Pat. No. 7,615,530, electrostatic layer by layer multilayer films provide a platform for immunogenic compositions for use as vaccines, for example. In an electrostatic layer by layer (LBL) multilayer film, deposition of oppositely charged polyelectrolytes onto a surface, such as a particle, provides a stable multilayer structure. Epitopes including polypeptide epitopes can be incorporated into a charged polyelectrolyte such as polypeptide, allowing for incorporation of a polypeptide epitope into the film. The films containing the epitopes can be used to elicit an immune response and provide protection against a target, such as a pathogen.

The process of electrostatic LBL fabrication is inherently repetitive. It involves coating the surface of a solid support, such as microparticles or nanoparticles, by immersion of the support in solutions of polyelectrolytes, followed by the elimination of excess soluble polyelectrolytes by a simple solvent exchange process, such as dialysis. In general, multiple immersion/elimination cycles are executed until a layer by layer film with desirable properties, for example, sufficient thickness or stability, is achieved. Many techniques can be used to execute repetitive LBL steps, but most suffer from undesirable conditions or they are difficult to automate. Automation of the LBL process is highly desirable because it replaces human actions, which are a well-known source of product variability. Additionally, if the LBL product is intended for use in humans or animals it is desirable that the process be conducted under aseptic conditions so as to avoid a terminal sterilization step that can damage the product. Accordingly, there is a need for automated tools and methods for coating particles using the LBL technique that can reproducibly and consistently produce a high quality product suitable for use in humans and animals.

SUMMARY

The above described and other problems and disadvantages of the prior art are overcome and alleviated by the present layer by layer ("LBL") construction of product by tangential flow filtration (TFF), or the like, including computer controlled automation of such procedure for production of a microparticulate constructs.

In one aspect, a system for automated synthesis of particles, the particles containing at least one polyelectrolyte layer deposited onto a substrate core, comprises
   a tangential flow filtration component comprising a TFF loop and a permeate valve, the permeate valve configured to selectively perform permeation steps via computer control, wherein the TFF loop comprises a particle reservoir for the substrate cores, a TFF filter, and a means for connecting the particle reservoir and the TFF filter; and
   a soluble reagent addition manifold component, wherein the delivery of the soluble reagent from the soluble reagent delivery manifold component to the tangential flow filtration component is controlled by at least one computer controlled valve, wherein the soluble reagent comprises the polyelectrolyte.

The above discussed and other features and advantages of the present disclosure will be appreciated and understood by those skilled in the art from the following detailed description and drawings.

BRIEF DESCRIPTION OF THE DRAWINGS

Referring to the exemplary drawings wherein like elements are numbered alike in the FIGURES.

DETAILED DESCRIPTION

Figure 1A:
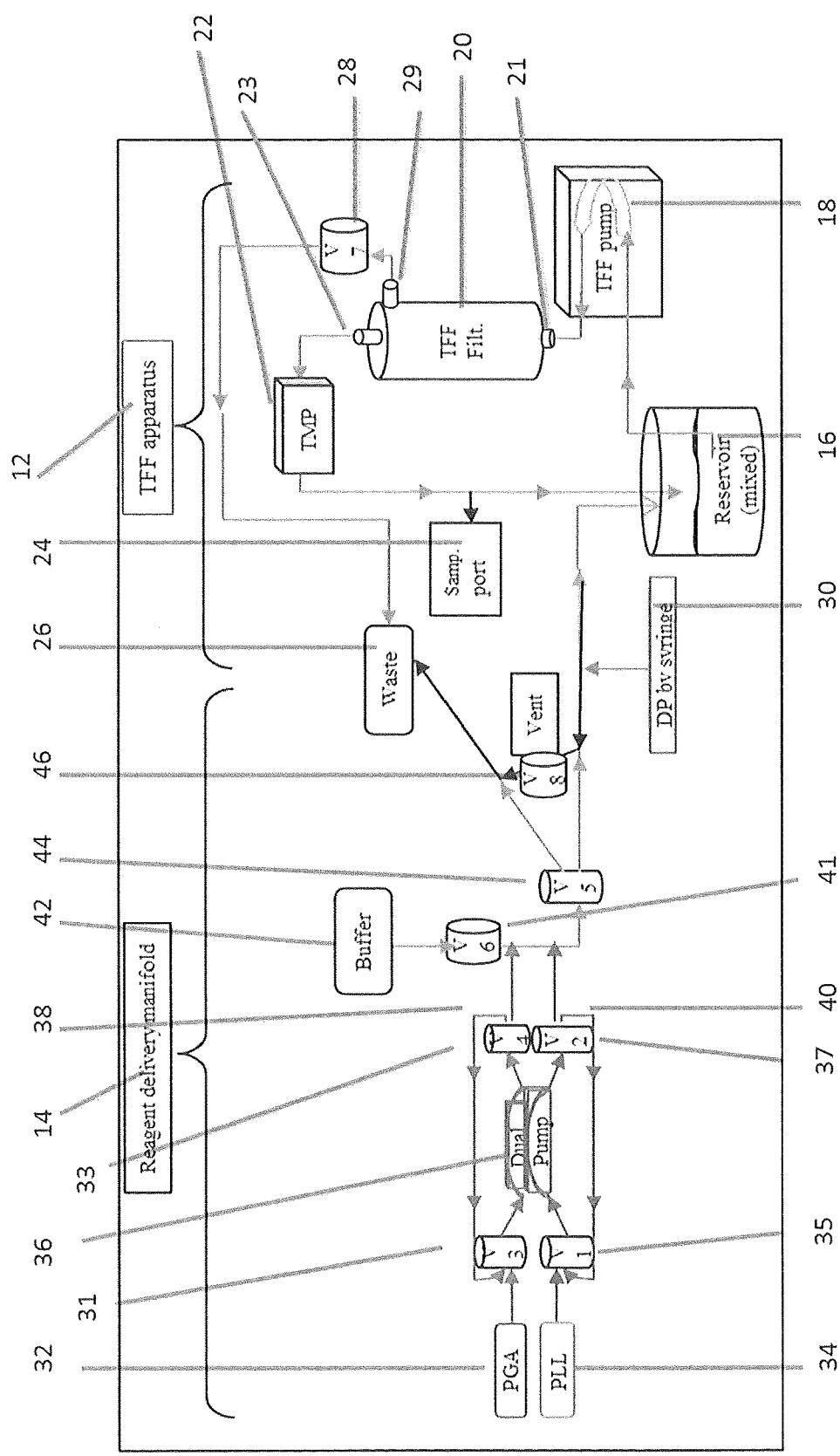
FIG. 1A illustrates a schematic drawing an exemplary LBL system equipped with a TFF apparatus.

Further to the brief description provided above and associated textual detail of each of the FIGURES, the following description provides additional details of example embodiments of the present disclosure. It should be understood, however, that there is no intent to limit example embodiments to the particular forms and particular details disclosed, but to the contrary, example embodiments are to cover all modifications, equivalents, and alternatives falling within the scope of example embodiments and claims. Like numbers refer to like elements throughout the description of the FIGURES.

It will be understood that, although the terms first, second, etc. may be used herein to describe various steps or calculations, these steps or calculations should not be limited by these terms. These terms are only used to distinguish one step or calculation from another. For example, a first calculation could be termed a second calculation, and, similarly, a second step could be termed a first step, without departing from the scope of this disclosure. As used herein, the term "and/or" includes any and all combinations of one or more of the associated listed items.

As used herein, the singular forms "a", "an" and "the" are intended to include the plural forms as well, unless the context clearly indicates otherwise. It will be further understood that the terms "comprises", "comprising,", "includes" and/or "including", when used herein, specify the presence of stated features, integers, steps, operations, elements, and/or components, but do not preclude the presence or addition of one or more other features, integers, steps, operations, elements, components, and/or groups thereof.

It should also be noted that in some alternative implementations, the functions/acts noted may occur out of the order noted in the FIGURES. For example, two FIGURES shown in succession, or steps illustrated within any given FIGURE, may in fact be executed substantially concurrently or may sometimes be executed in the reverse order, depending upon the functionality/acts involved.

Hereinafter, exemplary embodiments of the present invention are described in detail.

Layer by layer ("LBL") construction is a process in which a multilayer film is produced from alternating layers of oppositely charged polyelectrolytes, including, but not limited to, polypeptides. Polyelectrolyte multilayer films are thus thin films (e.g., a few nanometers to micrometers thick) composed of alternating layers of oppositely charged polyelectrolytes. Such films can be formed by layer by layer assembly on a suitable substrate, such as a flat substrate or a substrate core. In electrostatic layer by layer (LBL) self-assembly, the physical basis of association of polyelectrolytes is electrostatic attraction. Film buildup is possible because the polarity of the surface charge density of the film reverses on deposition of successive layers. LBL assembly of microparticulate constructs containing polypeptide layers is described, for example, in U.S. Publication No. 2012/0009254, incorporated herein by reference for its disclosure of LBL films containing polypeptides. While the exemplary processes herein employ charged polypeptide layers, charged polyelectrolytes other than polypeptides may be employed.

Figure 3A:
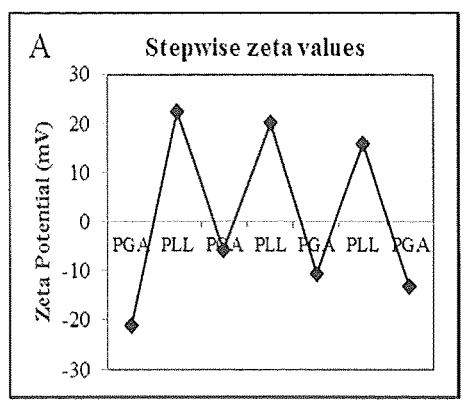
FIG. 3A shows stepwise zeta potential measurements on microparticles following LBL coating with homopolymers PLL and PGA. The alternating polarity pattern indicates successful LBL experiments.

According to current procedures, LBL assembly proceeds by the immersion of a solid support, such as a substrate core, in a solution of polyelectrolyte. The solid support bears a net surface charge, either positive or negative, and the polyelectrolyte bears a net charge opposite to that of the solid support. Driven by electrostatic attraction, the first polyelectrolyte assembles on the solid support surface. If enough of the first polyelectrolyte adsorbs to the surface, the surface takes on the polarity, either positive or negative, of the first polyelectrolyte. When that condition is achieved, the solid support can be immersed in a second polyelectrolyte, the net charge of which is opposite to that of the first polyelectrolyte. The second polyelectrolyte assembles on the surface of the solid support by electrostatic attraction and when sufficient polyelectrolyte is adsorbed, the net surface charge of the solid support will invert to its earlier polarity. The above steps can be repeated until an LBL film with desired properties, for example, sufficient thickness or stability, is constructed. The stepwise inversion of surface polarity, usually referred to as surface potential or zeta potential can be monitored and measured by analytical techniques such as dynamic light scattering (DLS). A graph of the stepwise DLS measured potentials in millivolts (mV) for a typical electrostatic LBL film construction is shown in FIG. 3A. Most of the exemplary LBL constructs provided below have 7 or 8 polyelectrolyte layers, but it should be understood that a construct can have as few as 2 polyelectrolyte layers or as many as 50 or more layers.

It is a common practice during LBL assembly to use excess soluble polyelectrolyte so as to saturate the surface of the solid support. Before the next oppositely charged polyelectrolyte can be introduced, the previous excess polyelectrolyte should be removed from the immersion solution. There are various ways to accomplish this task including dialysis, vacuum filtration, positive pressure filtration, centrifugation followed by aspiration, and others. All of these techniques suffer from various drawbacks that make them undesirable for use in a manufacturing process, especially if the product is intended for use in humans or animals.

In the case of dialysis, the LBL solid support, for example microparticles or nanoparticles, would need to be placed in a dialysis membrane bag or dialysis cassette following each LBL coating step. Such a process would be cumbersome, time consuming, and difficult to perform at large scale. It would also be difficult accomplish under aseptic conditions.

Repetitive LBL processing in a membrane filtration device has been described in the literature. In this process, substrate core suspensions, for example, microparticle suspensions are gently stirred over a small pore size filter membrane. Buffer and soluble reagents are driven through the membrane by either vacuum pressure from below or positive pressure by compressed gas from above while the particles are retained on the membrane. The purpose of the stirring is to prevent the particles from forming a cake layer, and to keep particles moving away from the membrane, which can clog the membrane pores. This process can be performed with minimal particle aggregation, but each step is slow and tedious, and it is likely that the process will not be practical at larger scale.

Centrifugation followed by aspiration of the supernatant and resuspension in buffer is a commonly used technique for performing LBL on substrate cores, particularly in research labs. An advantage of this approach is its simplicity because it can be performed in centrifuge tubes on a wide variety of commonly available centrifuges. Unfortunately, compaction of substrate cores during centrifugation often leads to aggregation. Additionally, scale up of a centrifugation process will generally require the processing of multiple tubes in parallel. This processing is cumbersome and provides an opportunity for chemical and biological contamination.

To summarize, the currently available methods of performing repetitive LBL cycles on suspensions of substrate cores suffer from one or more undesirable liabilities that include a predisposition to aggregation, time-consuming buffer exchange steps, excessive handling and/or transfer of the particles between steps, and opportunities for contamination. In addition, to our knowledge, the above methods have thus far only been performed manually and would be difficult to scale up and/or automate. This increases the opportunity of operator introduced variability and operator error. Thus there is a need for a scalable approach for synthesizing LBL particles in a closed system with a minimal amount of direct operator involvement.

Tangential flow filtration (TFF), also known as transverse flow filtration, is an established technique for the separation of species in a fluid mixture based upon differences in size. In TFF, a mixture is circulated across a membrane surface or through a hollow fiber filter under slight positive pressure. Herein the terms TFF membrane and TFF fiber filter are used interchangeably. The membrane contains pores of a defined size range that allow for solvent to move through the pores in a direction tangential to the flow of the mixture. Soluble or suspended species larger than the pore size, for example proteins, particles, or cells are retained. By continuously replenishing the solvent that permeates through the membrane pores, species or solutes smaller than the pore size are efficiently removed from the mixture without significantly changing the volume of the mixture. By judicious selection of the pore size, one can use TFF to separate low molecular weight solutes from proteins, soluble proteins from cells, or soluble polymers from microparticles and nanoparticles.

TFF separations can be performed using two-dimensional membranes over which the mixture is passed. Alternatively, separations can be performed using cylindrical fiber filters. The mixture is pumped across the inner surface of the cylinder. Aided by a pressure differential, solvent will pass through the fiber pores tangential to the flow of the mixture, carrying smaller solutes with it while solutes or particles larger than the pore size are retained within the cylinder An advantage of cylindrical fiber filters is that multiple fibers can be bundled in parallel, increasing the total filter surface area for increased permeation efficiency or increased scale. The fiber bundle or its equivalent is generally enclosed in a casing that includes an inlet port through which the mixture can enter the filter (21 in FIG. 1), an exit port through which the retained fraction can pass out of the filter (23 in FIG. 1), and a permeate port through which the permeate can exit the casing (29 in FIG. 1).

Figure 1B:
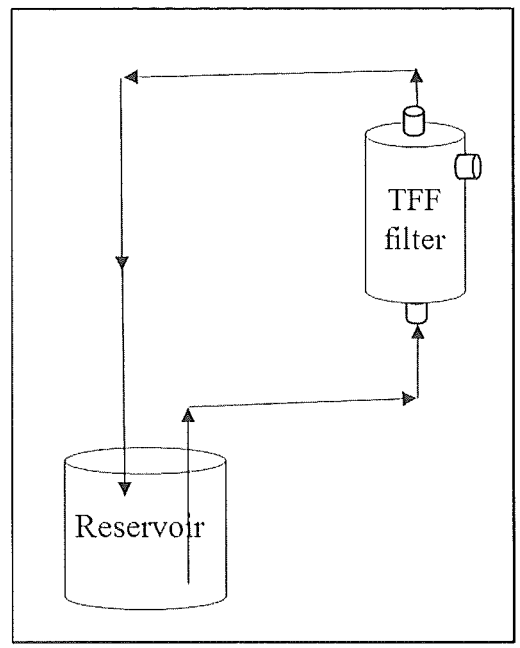
FIG. 1B is a schematic of a TFF circulatory loop.

A preferred practice during TFF is for the mixture undergoing filtration to be continually recirculated through the filter. A convenient way to accomplish this is to propel the mixture through a circulatory pathway that includes the filter. The most common method of propulsion is by a pump, for example a peristaltic pump. The pathway can be comprised of tubes, hoses, pipes, or similar conveyances. In most cases, the volume of the mixture undergoing filtration exceeds the volume capacity of the filter so at any time only a fraction of the mixture will occupy the filter. The pathway can also include a vessel that provides added volume and serves other functions as described in more detail below. Herein the vessel is referred to as the reservoir, or more specifically, the particle reservoir. The TFF filter and reservoir along with the connecting means (e.g. tubing) can be fashioned into the circulatory pathway and this assembly is referred to, herein, as the TFF circulatory loop. An example of a TFF circulatory loop is shown in FIG. 1B.

The TFF circulatory loop optionally can be augmented with other elements. For example a pump, a valve, multiple valves, ports, pathway branch points, scales, gauges, including pressure gauges, and other parts as needed for the particular application. It can also include multiple TFF filters arranged in parallel or in series, or multiple pumps, or multiple reservoirs arranged in parallel or in series. The TFF loop along with its various augmentations is referred to herein as the TFF apparatus, or optionally the TFF component, and an example is shown as item 12 in FIG. 1. As will be described in more detail below, the TFF pump and one or more valves that control various aspects of the process can be external to the TFF circulatory loop, that is, they do not come in direct contact with the mixture passing through the loop.

The fraction of solvent that passes through the pores of a TFF membrane or fiber filter and exits the circulatory loop is called the permeate. Permeate often carries solutes out of the circulatory loop, provided that they are small enough to pass through the pores of the TFF membrane. As described above, TFF filter fibers are usually encased so that permeate collects within the casing and can pass out through a port. The flow of permeate through the port can be restricted or stopped with a valve or a clamp. Herein, a valve the controls the flow of permeate out of a TFF filter is called the permeate valve, and an example is displayed schematically as item 28 in FIG. 1.

In addition to the TFF loop, the tangential flow filtration apparatus described herein comprises a permeate valve, wherein the permeate valve configured to selectively perform permeation steps via computer control.

Permeation is the process of removal of solvent from the TFF circulatory loop by passing through the pores of a TFF membrane. Permeation occurs when the permeate valve is opened (for example 28 in FIG. 1) and there is pressure differential across the TFF membrane. The pressure differential across the membrane is referred to as the transmembrane pressure (TMP). Positive pressure is generated on the upstream luminal side of the filter by the TFF circulatory loop pump and may be sufficient to induce permeation. However, often the pressure should be increased to generate a desired rate of permeation. This can be accomplished by introducing a constriction in the circulatory loop (22 in FIG. 1). For instance, partial pinching of the circulatory tubing downstream of the TFF filter (20 in FIG. 1) will cause TMP to increase and an increase in permeation rate.

In one aspect, the tangential flow filtration component comprises a metering device to measure an amount of permeate that passes through the filter during a particular polyelectrolyte deposition cycle step and reports that data back to the controlling computer. For example, the computer control can automatically terminate a polyelectrolyte deposition cycle step upon measuring a user specified amount of permeate. Optionally, the indication is in the form of a signal from an electronic scale that continually measures the amount of permeate that exits the tangential flow filtration loop.

When the permeate valve is opened and no new replacement buffer is introduced, the system volume decreases by the amount of permeate that is removed. This is often referred to as a concentration step. When new buffer is continually introduced to the system during permeation, the system volume remains nearly constant. This is often referred to as a buffer exchange step or a washing step.

The fraction of solvent, solutes, and suspended particles that do not pass through the TFF membrane and are retained in the circulatory loop is referred to as the retentate. The retentate can exit the TFF filter via a port, for example 23 in FIG. 1 and return to the reservoir from where it can be recirculated through the TFF filter.

The continuous movement of solvent, solutes, or suspended solids through a circulatory loop is referred to as recirculation. The movement is driven by a pump, for example, a peristaltic pump (for example, 18 in FIG. 1). When the solvent contains both soluble polyelectrolytes and a suspended substrate such as microparticles this is also referred to as an LBL coating step, or optionally, a deposition step. The adsorption of a polyelectrolyte, for example, a homopolypeptide, to a substrate core followed by elimination of excess polyelectrolyte constitutes an LBL cycle, or a polyelectrolyte deposition cycle.

Solvent is defined herein as the fluid or fluid mixture that carries the mixture of solutes or suspended particles, or cells, or combinations of these through various pathways. The solvent is often an aqueous buffer, generally at or near neutral pH. Herein the terms solvent and buffer are used interchangeably.

When the TFF permeation valve is closed, the mixture can be, and often is recirculated through tubing from the reservoir, through the pump, through the TFF filter, and back to the reservoir, that is, through the TFF circulatory loop. In most applications, the circulatory loop also passes through a device to regulate transmembrane pressure. Using junctions and valves, reagents can be introduced to the circulatory loop in an efficient and well-controlled manner. For example, concentrated solutions of polyelectrolytes or polypeptides can be delivered to the circulatory loop in this fashion. The reagent solutions are rapidly dispersed throughout the TFF loop by the dynamics of recirculation, and dispersion can be assisted by mechanical stirring of the reservoir. Thus, the circulatory loop is a convenient and desirable environment for conducting chemical steps on a mixture, for example, the coating of microparticles with soluble polyelectrolytes A key feature of TFF is that solutes and/or particles within the circulatory loop are kept in constant motion if desired, and in controlled and nearly constant volume. In the specific application of adsorbing polyelectrolytes to nanoparticles or microparticles during LBL fabrication, this is advantageous because it facilitates even coating of the particle surfaces. Additionally, it helps to prevent particles from sticking together and forming undesired aggregates. Optionally, the tangential flow filtration component comprises a volume metering device configured to report TFF circulatory loop volume data to a controlling computer. In this embodiment, the system optionally comprises a controlling computer configured to maintain the loop volume of the mixture inside the tangential flow filtration component to within a set range by activation of a valve or multiple valves to either increase the volume by addition of a reagent or decrease the volume by permeation.

Another key aspect of TFF is that the mixture being manipulated recirculates in a loop from a reservoir through a pump, across the TFF filter, and then back to a reservoir. If the pump is external to the flow stream and does not come in direct contact with the contents of the loop as is the case for example with peristaltic pumps, the mixture is protected from external contamination such as dust, chemicals, or biological contaminates such as virus particles, fungi, or bacteria. Likewise, if the various clamps and valves that control the direction of the mixtures, that modulate the transmembrane pressure, and release permeate are external to the flow stream, as is the case with pinch valves, they too are physically separate from the contents of the loop and the mixture is protected from external contaminates. Thus the TFF circulatory loop reservoir, TFF filter, and the connecting means can constitute a closed system where its contents are protected. If one wishes to conduct LBL by TFF under aseptic conditions, for example, to make a product suitable for use in humans or animals, such a closed loop can be constructed and then sterilized by treatment with heat, radiation, or chemicals. The sterile closed loop is then mounted on to the TFF pump and valves. The great advantage of this approach is that to achieve an aseptic environment, only the loop materials require sterilization, the external hardware does not.

Figure 12:
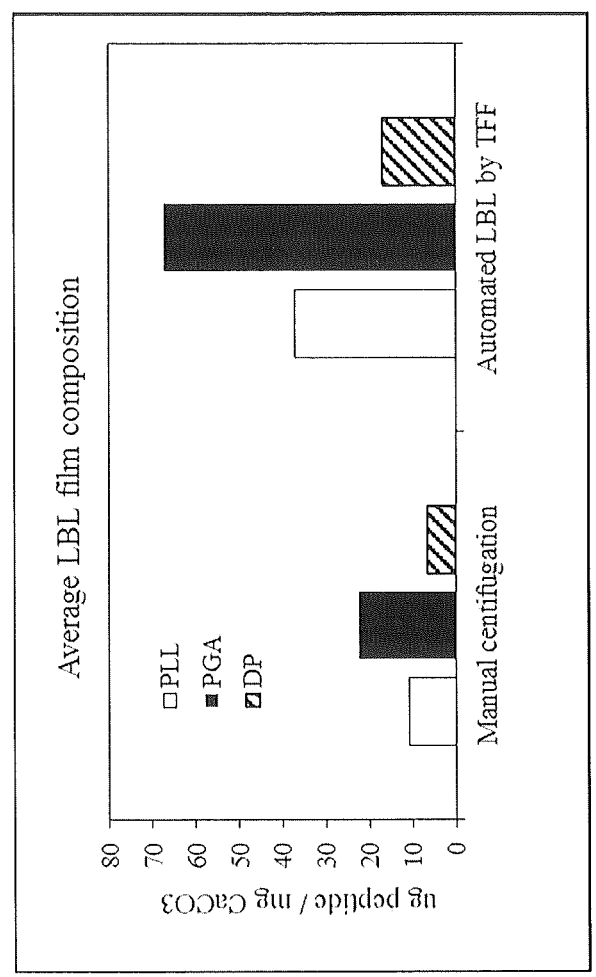
FIG. 12 shows the average PLL, PGA and DP amounts incorporated into microparticle constructs using either the manual centrifugation/aspiration/resuspension method or the LBL by TFF method.

As will be described in more detail below, for the purpose of performing LBL by TFF one or more various reagents are dispensed from a soluble reagent addition manifold component to the TFF circulatory loop using at least one computer controlled valve. The reagent deliveries are controlled by various valves and one or more pumps. Again, if pinch valves and peristaltic pumps are used they do not directly contact the reagents and the reagents are protected from external contaminates. The tubing network that conveys the reagents and various vessels that hold the reagents can be assembled, sterilized by appropriate treatment, and then mounted to the reagent addition manifold hardware. A primary embodiment of the invention is that the reagent delivery manifold is connected to the TFF component. This connection can be a simple tube or hose that conveys the output of the reagent manifold to a part of the TFF circulatory loop, for example the TFF reservoir, The use of TFF as a platform for performing LBL appears to have another advantage over other approaches. For example, multiple experiments have shown that the amount of homopolypeptides PLL and PGA deposited into a film is 100%-250% higher with the TFF method than that observed using the manual centrifugation/aspiration/resuspension method. The higher efficiency of LBL by TFF appears to be a general phenomenon and is illustrated in Example 4 and FIG. 12. Higher efficiency is desirable for a number of reasons. First, polypeptide polyelectrolytes are expensive. Greater capture of these valuable reagents in the film means less peptide is lost to the permeate and eventually discarded. Second, it is well known from work with non-peptide polyelectrolytes that film stability correlates with the degree of film deposition, sometimes referred to as film thickness. Thicker films are expected to have longer storage lifetimes and other properties of biological relevance. Additionally, more efficient LBL means that a desired film thicknesses will be attained faster, perhaps enabling the repetitive LBL by TFF process to be shortened by one or several cycles. Automation of the LBL by TFF process expands the impact of this advantage by making film deposition more predictable and reproducible.

In relevant part, the present disclosure relates to LBL construction of products by tangential flow filtration (TFF), also known as transverse flow filtration or the like. In particular, the present disclosure relates to the automation of such procedure, itself, and as it relates to scalability of manufacture of products, which in exemplary embodiments, includes microparticulate and nanoparticulate constructs.

As will be described below, one or more various reagents are dispensed using computer control, into the TFF loop (for example reservoir 16 in FIG. 1), according to a computer system in order to provide the desired microparticulate product. In exemplary embodiments, the LBL by TFF process is used to prepare a high quality microparticle vaccine construct, though of course, this is merely an exemplary product.

In exemplary embodiments, each LBL cycle is performed under computer control. While all reagent dispensing is contemplated as being automatic, that is, without direct user action, it should be noted that, if desired, some user intervention may be contemplated. For example, a user may wish to pause the process for another purpose, such as removing a sample for analysis to ensure that a step has been completed satisfactorily before continuing the process.

In the present disclosure, we will refer to processes, methods and systems as automated or semi-automated LBL by TFF, meaning one or more steps is computer controlled.

In one aspect, tangential flow filtration component and said soluble reagent delivery manifold component are configured to perform automatic layer by layer formation of multilayered films containing a plurality of oppositely charged polyelectrolyte layers, wherein at least one polyelectrolyte deposition cycle is at least partly automated by computer control of tangential flow filtration permeation steps and by computer control of delivery of plural reagents from said soluble reagent delivery manifold component.

Specifically, in one aspect, a system for automated synthesis of particles, the particles containing at least one polyelectrolyte layer deposited onto a substrate core comprises a tangential flow filtration component comprising a TFF loop and a valve, the valve configured to selectively perform permeation steps via computer control, wherein the TFF loop comprises a particle reservoir for the substrate cores, a TFF filter, and a means for connecting the particle reservoir and the TFF filter; and a soluble reagent addition manifold component, wherein the delivery of the soluble reagent from the soluble reagent delivery manifold component to the tangential flow filtration component is controlled by at least one computer controlled valve, wherein the soluble reagent comprises the polyelectrolyte.

In such a way (though it should not limit the present disclosure), it may be advantageous to consider the apparatus as including two major components, the TFF circulatory loop and a soluble reagent addition manifold. Referring now to FIG. 1, we see such a division, with the TFF loop illustrated generally at 12, and with the reagent delivery manifold illustrated generally at 14.

In one aspect, the permeate valve and the computer controlled valve of the soluble reagent addition manifold component are fully automated. Herein, a fully automated valve is an electronically operated valve that is activated, for example, opened or closed, under computer control and without user initiation.

Specifically, in embodiments described herein, referring to FIG. 1, an exemplary TFF loop includes particle reservoir 16, TFF pump 18, TFF filter 20, TMP pressure regulator 22, with the loop returning to reservoir 16. Permeate valve 28 controls the release of permeate from the TFF filter to a waste receptacle 26. In exemplary embodiments, a computer that accompanies the TFF monitors filter pressures and permeate volume and may selectively issue instructions to the device. As in the illustrated exemplary embodiment, the TMP to reservoir path may include a sample port 24.

Figure 6:
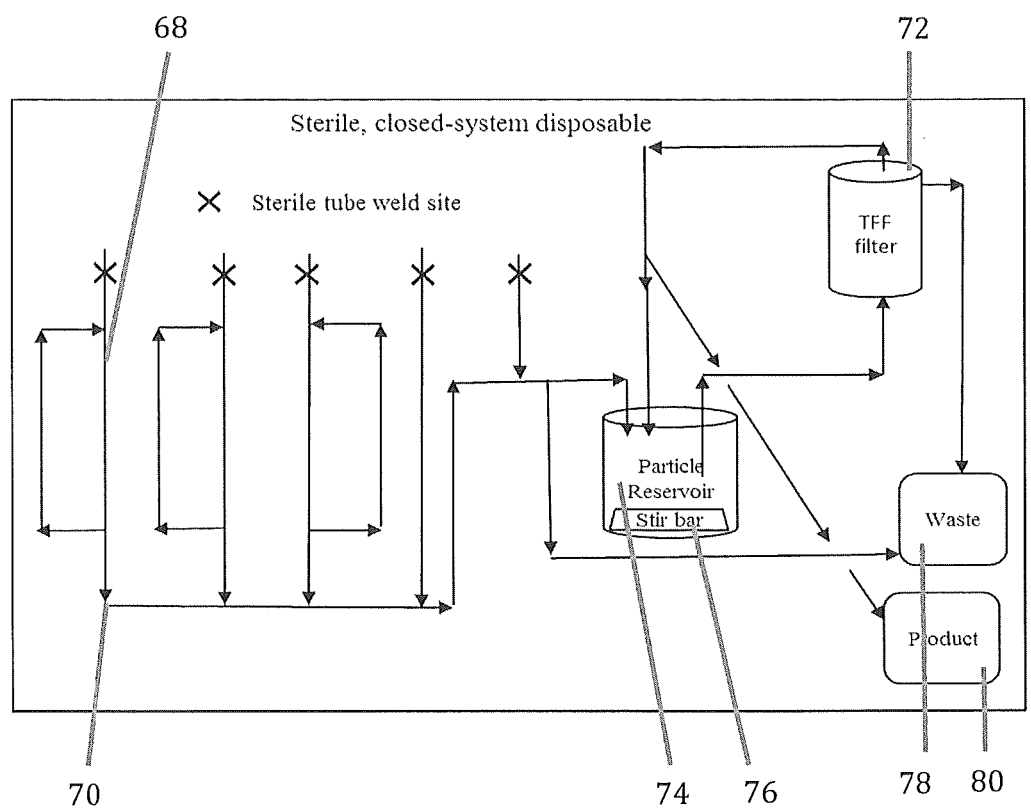
FIG. 6 provides a schematic for the closed loop tubing network to be assembled then mounted on the system illustrated in FIG. 5.
Figure 11:
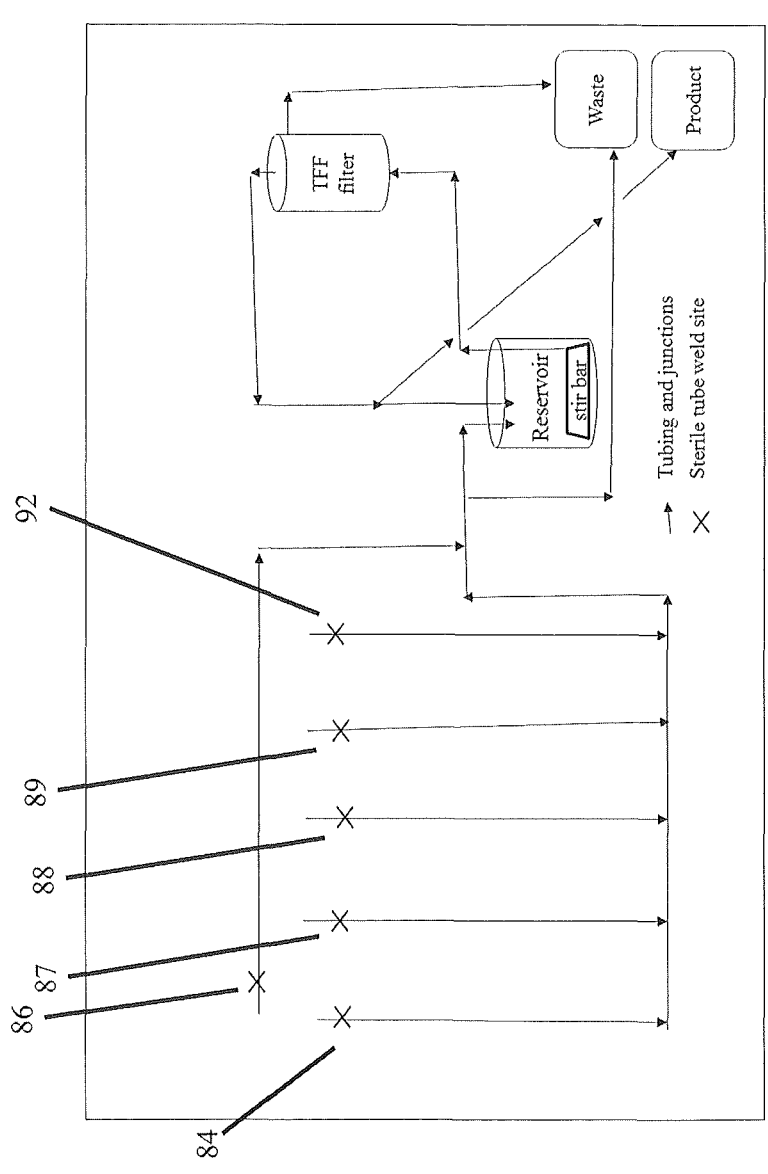
FIG. 11 is another closed loop tubing network designed to mount to the apparatus shown in FIG. 10.
Figure 15:
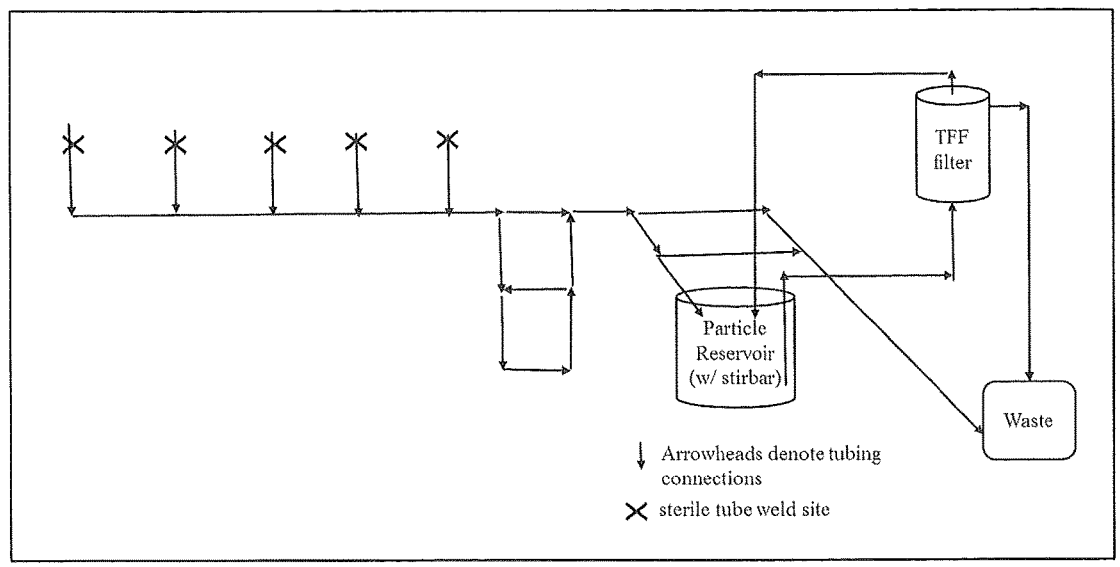
FIG. 15 is a schematic diagram for the disposable tubing network that can be assembled and sterilized before mounting to various pinch valves and clamps shown in FIG. 13 and FIG. 14.

In one aspect, the system provides a continuous flow path for synthesis of particles. Optionally, the permeate valve, the computer controlled valve of the soluble reagent addition manifold component and optional pumps in the system are external to the continuous flow path. That is, these components do not come in direct contact with the contents of the TFF circulatory loop or any of the soluble reagents delivered from the addition manifold. The continuous flow path is comprised of the TFF filter, the particle reservoir, and the connecting means. The continuous flow path optionally comprises tubing segments and junctions, including 3-way junctions that connect the reagents to the TFF circulatory loop. The examples of closed-loop tubing networks shown in FIG. 6, FIG. 11, and FIG. 15 are also examples of continuous flow paths.

In exemplary embodiments, the TFF loop 12 is charged with a $CaCO_3$ particle suspension that is kept in constant recirculatory mode throughout the process. The turbulence created by the flow of particles through the loop may be sufficient to keep a well-dispersed suspension. Alternatively, mechanical stirring of the suspension in the particle reservoir can be added to ensure good dispersion.

The the delivery of the soluble reagent from the soluble reagent delivery manifold component to the tangential flow filtration component is controlled by at least one computer controlled valve. In FIG. 1, the computer-controlled valve is V5 at (44). In one aspect, the soluble reagent delivery manifold component comprises plural computer controlled valves for delivery of plural reagents. The plural soluble reagents include oppositely charged polyelectrolytes, for example. In certain aspects, the soluble reagent delivery manifold component comprises computer controlled delivery of a washing buffer either to waste, to the tangential flow filtration component, or both.

Aside from the $CaCO_3$ microparticle suspension, which may be manually, or in exemplary embodiments, automatically introduced before LBL steps, the soluble reagents added during stepwise TFF via the soluble reagent addition manifold component may be, for example, concentrated polyelectrolyte stock solutions, and washing buffer.

There are multiple ways that reagents can be propelled from the soluble reagent manifold component (automated in part or in whole), to the TFF circulatory loop including pumping, gravity, syringe, or compressed gas. Of these methods, peristaltic pumping and gravity provide good compatibility with sterile, closed-loop systems. In one aspect, the soluble reagent delivery manifold component comprises at least one pump configured to propel the soluble reagent through a path containing one or more computer activated valves to the particle reservoir.

When using peristaltic pumps for reagent delivery, one can use separate pumps for each reagent or a single pump with separate pump heads or separate channels on a single pump head for each reagent. The advantage of separate pumps is that each can be activated independently of the other and pump speeds can be independently varied. The main disadvantages of separate pumps are their cost, their size, and the need for individual electronic control. The main advantage of a single pump with multiple heads or multiple channels is that it reduces the number of separate pumps that need be added to the reagent delivery manifold. This reduces costs and overall size of the device, potential sources of process failure, as well as simplifying the electronics design and computer control commands. In a multiple channel configuration, the reagents can be recirculated at a desired velocity in a loop and can be delivered to the TFF loop at the time and in the quantity desired by opening one or more pinch valves for a fixed time period. One can appreciate that the two approaches are interchangeable and a practitioner can choose the one which best fits the purpose.

For exemplary embodiments, electrically activated pinch valves are contemplated, e.g., 2-way and 3-way valves from Cole Parmer, Inc. because of their simplicity and adaptability to different tubing sizes and materials. Moreover, pinch valves do not come in contact with the solutions moving through the tubes and as such cannot contaminate the contents of the tubes. Pinch valves are excellent valves for controlling the delivery or circulation of volumes from about 1 mL to 100 L. Larger valves with different designs can be supplanted for control of larger volumes of about 0.1 L to 1000 L, or more. A 2-way valve toggles between on and off, or open and closed. By convention, a tube running through a 2-way valve is pinched or closed when off, not pinched or open when on. The valve is turned on by supplying DC power to the valve, and this is readily controlled by a relay board and if desired, a computer. With a 3-way valve there is a T or Y junction that splits the tubing in either of two directions. When the valve is off one of the directions is pinched closed with a piston, the other direction is open. When the valve is turned on by supplying DC power, the piston moves, opening the first line and closing the second.

In one aspect, the soluble reagent delivery manifold component comprises a reagent metering device configured to indicate the volume or weight of delivered or undelivered soluble reagent. The metering device optionally is configured to transmit data to a computer for the purpose of recording the times and amounts of delivered soluble reagent.

Relay boards, power supplies, and peristaltic pumps are useful for exemplary reagent delivery manifolds. The wiring of the various pinch valves, so that they may be controlled by a computer, can be assembled by someone with reasonable electrical and technical skills using readily available electronics supplies. The valves and DC power required to run the valves are wired to a multi-channel relay board that in turn connects to a computer via a USB cable. Readily available software that is sold with the relay board is used to write the sequence of commands that are sent to the relay board which turns on or off specific valves at desired time sequences.

The following describes a possible exemplary configuration for reagent delivery:

For delivery of the oppositely charged homopolypeptides (HPs) poly-L-glutamic acid (PGA) (32 in FIG. 1) and poly-L-lysine (PLL) (34 in FIG. 1), one option is a single peristaltic pump with dual pump heads (36). Because the pump heads are coupled, they both run at the same speed with each head pumping its respective reagent at the desired flow rate (note that this is merely an exemplary embodiment). Using two 3-way valves for each reagent, for example PGA is controlled by valves V3 and V4 (31 and 33 in FIG. 1), and PLL is controlled by valves V1 and V2 (35 and 37 in FIG. 1), a dual head pump may be run at a single speed throughout the TFF process.

Before commencing with LBL cycles, the lines that convey the HPs PLL and PGA may be primed with HP stock solutions. Priming is accomplished by computer instructions that alternatively open and close 3-way valves V1-V5 (31, 33, 35, 37, 44).

In exemplary cases, most of the time, the HP stock is recirculating through a short loop around and through the pump head. When an aliquot of HP solution is required for the next LBL step, the 3-way valves for that pump head are switched to the main manifold and a bolus of reagent is driven to the TFF loop particle reservoir (16 in FIG. 1). Referring to FIG. 1, when valves V1-V4 (31, 33, 35, 37) are in the switched off, the solutions in the lines recirculate through the loops. When delivery of an aliquot of PLL solution to the TFF loop is required, valves V1, V2, and V5 (35, 37, 44) are actuated by computer control, redirecting PLL solution to flow through the outlet and to the particle reservoir. When the correct amount is delivered the valves are turned off and the PLL returns to recirculatory mode. Advantages of this approach include the fact that a single multi-head pump running at a set speed can be used to deliver up to four separate reagents without instructions to the pump from a computer.

The factors that determine whether the desired amount of reagent is delivered to the recirculatory loop are the speed of the pump, the diameter of the tubing, the period of time that the requisite valves are open for delivery, and the length of the path from the pump to the circulatory loop. This last factor is often referred to as the dead volume, and it must be considered and accounted for when developing a method for reagent delivery. In general, the dead volumes will be filled or primed with washing buffer at the time a regent is directed to the circulatory loop and will be replaced with reagent solution during the addition step with V5 and V6 (42 and 44 in FIG. 1). This volume can be driven into the loop by buffer or displaced to a waste receptacle, again by buffer. Generally, the dead volumes will be flushed to waste so as not to unnecessarily dilute the recirculation volume, except when it is a particularly valuable reagent such as a chemically synthesized polypeptide. In this case it can be pushed into the circulatory loop with buffer by activating the appropriate valves. Dead volumes can be minimized by using shorter tubing lengths or tubing with small diameters as is practical for a particular application. In certain cases, the dead volumes may be only equal to a small amount, for example 1%-5% of the total amount delivered, and sometimes can be ignored. In order to assure that accurate volumes of reagents are delivered, the pump speed and valves are calibrated.

Typically, a pump speed is chosen so that an HP delivery can be accomplished in a short period of time, typically less than a minute. For example, if an aliquot of 5.0 mL of PLL is desired, a convenient pump speed may be one that delivers 40 mL/min (0.667 mL/sec). At that pump rate, opening of valves V1, V2, and V5 (35, 37, 44 in FIG. 1) for 7.5 seconds will deliver 5.0 mL into the path towards the reservoir. Of course, the actual amount that reaches the reservoir may be less than 5.0 mL because of the dead volume along that path. If the measured dead volume was 1.0 mL, then the time the values are opened can be increased to 9.0 seconds, and 5.0 mL will reach the reservoir and 1.0 mL will remain in the dead volume path, and eventually flushed to waste. Or as mentioned above, the dead volumes can be minimized to the point where they are insignificant compared to the delivered volume.

Advantageously, the soluble reagent (e.g., polyelectrolyte) is delivered to the tangential flow filtration component and well mixed so that a polyelectrolyte concentration is predictable and reproducible. During system testing, the actual volumes delivered are optionally measured to confirm that desired amount and the pump speeds and or valve open times are adjusted accordingly. In general, it is a straight-forward task to calibrate deliveries of polyelectrolyte to within +/−20% of the desired amount. Indeed accuracies to within +/−10% or even +/−5% are readily attainable. As discussed above, LBL coating of substrates with HPs, for example, is often performed with excess peptide so that the substrate is saturated with HP. Under saturation conditions, the amount of HP deposited during an LBL coating step is relatively insensitive to fluctuations in the concentration of the HP solution. Thus, the accuracy of reagent delivery is often not critical to the quality of the product and delivery accuracies of about +/−20% may be sufficient. For other steps, particularly those where deposition is performed at concentrations below saturation, a higher level of accuracy may be required. In certain aspects, the desired polyelectrolyte, e.g., polypeptide, concentration is about 0.2 to 2.0 mg/mL.

While the above describes dual-headed pumps and recirculatory loops, other embodiments are contemplated herein, for example individual pumps for each reagent, no recirculatory loops, etc. At larger manufacturing scales, such configurations may be preferred. The key aspect of either approach is that under computer control the correct reagent is delivered to the TFF circulatory loop at the desired time and in the desired quantity.

The TFF circulatory loop (12 in FIG. 1) is coupled to the reagent delivery manifold (14). This coupling can occur anywhere along the loop, and in this version of the current invention, coupling is at the TFF reservoir (16). The TFF circulatory loop can be assembled from various available components by one well skilled in the art or purchased as a whole unit from a vendor. Suitable systems are sold by Spectrum Labs (Rancho Dominguez, CA) or Pall Corporation (Port Washington, NY), and these systems can be operated at a wide range of scales. For example, the KrosFlo® Research II system sold by Spectrum labs is suitable for 0.002-10 L scale while the KrosFlo® Pilot Plus system is suitable for scales of 10-5000 L.

Referring to FIG. 1, exemplary components of a TFF apparatus are the TFF pump (18), a transmembrane pressure device (TMP, 22), permeate valve (28) and the TFF circulatory loop including the TFF filter (20) or filter membrane, a permeate outlet (29), and particle reservoir (16). The TMP device creates a pressure differential between the inner and outer surfaces of the TFF filter and enhances the flow of permeate across a filter fiber or a membrane. TMP can be increased or decreased as desired to increase or decrease the rate of permeate flow through the pores. The rate of permeate flow is often referred to as the flux rate and is measured in terms of unit volume per unit filter surface area per unit time. For example, a flux rate of 1.0 liter per square meter per hour ($L/m^2/h$) or 1.0 LMH means that a fiber filter with a 1.0 $m^2$ surface area will produce 1.0 L of permeate in 1.0 hour.

The permeate port (29 in FIG. 1) and valve (28) allow permeate to exit the TFF circulatory loop. When the permeate valve is closed, the contents of the TFF system recirculate and the volume is usually kept constant. The recirculating volume is often referred to as the retentate. It is also referred to as the TFF loop volume. When the valve is open permeate is allowed to pass through the TFF fiber filter pores (20 in FIG. 1). When no additional reagents or buffers are being added to the system, the total volume of the retentate is reduced by the amount of permeate exiting the system. This is referred to a concentration step and is useful during LBL to bring the total system volume, which may have increased due to the addition of HP solution, DP solution, or buffer, back to its desired level.

The TFF pump drives the retentate through the TFF circulatory loop. It is often a peristaltic pump with adjustable pumping speed. The speed can be set for a desired effect, such as uniform mixing of the retentate, or to achieve a certain filter surface shear rate so as to minimize fouling. Peristaltic pumps are desirable because they are external to the loop and do not come in direct contact with the contents of the loop, and as such are useful for aseptic processing. Syringe pumps or piston pumps can also be used, but since they contact the loop contents directly, they generally require special cleaning and sterilization procedures to make them suitable for aseptic processing.

The TFF circulatory loop reservoir (16 in FIG. 1) serves a variety of purposes. First, the reservoir volume can be large or small but often it is useful for its volume to be larger than the volume of the rest of the TFF circulatory loop. Under this condition, most of the retentate will occupy the reservoir at any particular time so it is a convenient location to add reagents, especially for the purpose of conducting a chemical step such as LBL film fabrication. If the flow rate of the TFF pump is sufficient, it can create enough turbulence in the reservoir to keep its contents well mixed but if additional mixing is desired it can be equipped with a mechanical stirring system such as, for example, a magnetic stir bar (for example stir bar 76 in FIG. 6), an overhead mechanical stirrer, an orbital shaker table, or other to keep the contents of the reservoir well mixed. In addition, as the rest of the TFF loop is filled with retentate the reservoir can provide ballast and accommodate increases or decreases in retentate volume that occur during processing. These changes in volume can be actively managed as described below.

A key aspect of automated coating of substrate cores (e.g., LBL) by TFF is the ability to control and maintain the volume of particle suspension that circulates through the TFF loop. In general it is desirable to maintain this volume near a constant level throughout the entire process. In practice, there are fluctuations in the total TFF circulatory loop volumes. Delivery of an aliquot of HP solution to the TFF loop increases the overall volume by that amount. It is generally undesirable to increase the volume cumulatively throughout the LBL steps, so one may choose to subtract that volume during a concentration step, for example, at the front end of the subsequent permeation step. This can be performed by opening an exemplary permeate valve (28 in FIG. 1) with the washing buffer supply valve (41) closed until the volume has returned to its previous volume. Concentration steps can be incorporated into automated LBL cycles and executed under computer control.

In exemplary experiments, programmed adjustments to the TFF loop volume are avoided because the loop volume has been found to be self-regulating. An example of this is described in Example 3. To a starting volume of about 20 mL $CaCO_3$ particles was added a 5.0 mL aliquot of PLL solution. Since the addition was made while the permeate valve (28 in FIG. 1) was closed, the total retentate volume increased to about 25 mL. After five minutes of recirculation, the permeate valve V7 (28) is opened and about 5 mL of permeate exit the filter to waste. The driving force for this first bolus of permeate is a slight increase in pressure that is caused by the PLL addition. The buffer supply valves V5 and V6 (44, 42) are then opened to allow the inflow of buffer. Permeate leaving the system creates a small vacuum in the particle reservoir which draws buffer in. As long at the TFF loop is not vented, the temporary fluctuations in loop pressure act to regulate the TFF loop volume to about 18-25 mL per cycle.

The self-regulation of TFF loop volume described above may not be sufficient at higher manufacturing scales. In some cases, TFF system volume may need to be actively managed by concentration or buffer addition steps. Automated regulation of retentate volume may require electronic monitoring and reporting of retentate volume to computer control. Optical sensors or digital scales (for example 94 in FIG. 10) can be used to report TFF loop volume information to a computer. The computer then responds in real-time, increasing or decreasing the retentate volume by opening and closing appropriate valves until the target volume range is reached. Such control may require additional wiring for the sensor and computer routines that can be provided by an electrical engineer normally skilled in the art.

For the manufacture of sterile products, it is advantageous that all of the steps be conducted in a sterile closed-loop system so as to exclude chemical and biological contaminants such as bacteria. During reagent addition steps, suspension concentration steps, and other operations, the circulatory volume in the TFF loop can either increase or decrease. Under closed system conditions, this can create fluctuations in system internal pressure, which may change the dynamics of the TFF process in undesirable ways. Such changes are revealed during methods development and testing, and can be managed. For instance, vent lines can be added to the tangential flow filtration component and/or the soluble reagent delivery manifold and operated with pinch valves (46 in FIG. 1). Optionally, the vents are computer-controlled vents. The venting can be to the external environment through a sterile filter membrane or internally to a ballast volume in the form of a diaphragm or collapsible bag, or other approaches can be devised that protect the system from contamination. An example of an internal vent is valve V10 in FIG. 13 which allows excess pressure to escape to the waste receptacle. Venting steps can be added at predefined times to an automated process when desired. Alternatively, pressure transducers can provide live feedback to a controlling computer, which can respond and maintain pressure within a user defined range by opening or closing venting valves. In other cases, the fluctuations in pressure are desirable and no venting is required. For example, in the self-regulating system described above, permeate exiting the system creates a slight vacuum that draws replacement buffer into the particle reservoir without need for pumping or metering. Thus, whether active management of internal loop pressure is necessary will depend upon the scope and scale of the process.

Referring again to FIG. 1, the delivery manifold (14) and the TFF circulatory loop (12) are illustrated as an exemplary configuration. In this exemplary embodiment, eight valves (V1-V8) are computer controlled and operated by simple custom written code. Soluble HPs PGA (32) and PLL (34) are pumped by a dual-head peristaltic pump (36) and recirculate through short loops (38, 40) until called for by the computer, which activates the appropriate 3-way valves V1-V4 (31, 33, 35, and 37). Washing buffer is, in this case, delivered by gravity through valve V6 (42) to either waste or by suction to the particle reservoir through valve V5 (44). As was discussed before, DP may be delivered via syringe (or automatically) during the final LBL step at a port (30) in the inlet line. In the TFF loop, the particles can recirculate continuously throughout the process. Permeation (washing) steps may be controlled by valve V7 (28). Particle suspension samples may be collected for analysis as desired during each LBL step via a syringe at an exemplary sample port (24).

An exemplary process follows:

EXAMPLE 1

Precipitation of $CaCO_3$ Microparticles for use as Substrate Cores

Figure 3B:
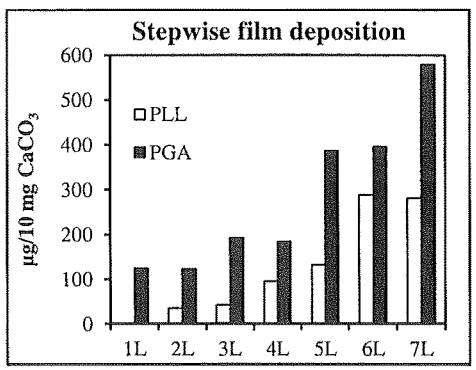
FIG. 3B shows exemplary stepwise LBL film deposition as measured by amino acid analysis (AAA)

A modified version of precipitation methods known in the art was used. To a rapidly stirred solution of 20 mL 0.33 M $Na_2CO_3$ containing 1.0 mg/mL poly-L-glutamic acid, sodium salt (Sigma-Aldrich cat# P4636), was added 20 mL of 0.33 M $CaCl_2$. The precipitated $CaCO_3$ microparticle mixture was stirred at 700 rpm for 40 seconds. Particles were examined under a microscope at 40× magnification and were found to be mostly spherical particles 3-4 µm in diameter. The suspension was transferred to a centrifuge tube and spun at low speed until all the visible particles were pelleted. The supernatant was aspirated and the particles were suspended in 20 mL of 10 mM HEPES buffer pH 7. The particles were spun again, the supernatant aspirated, and then suspended again in 20 mL HEPES buffer. The resulting 3% $CaCO_3$ suspension was used directly in a subsequent LBL experiment or stored at 4° C. and used within several days. Microparticles prepared by this procedure contain PGA as the first HP LBL layer, and this was confirmed by measuring the zeta surface potential of particles suspended in pH 7.0 buffer (FIG. 3A) and by amino acid analysis (FIG. 3B). Typical zeta potential values are about −15 to −30 mV as measured on a Zetasizer from Malvern Instruments.

EXAMPLE 2

Semi-Automated Control of HP PLL Delivery and Subsequent Elimination of Excess HP by TFF Permeation An apparatus constructed essentially as described in FIG. 1 was used. The pinch valves were connected via a relay board to a DC power supply. Distribution of the power to the valves was controlled by a computer connected to the relay board. Code was written to execute the various valve instructions. The TFF loop consisted mainly of the Kros- Flo® Research II TFF system (Spectrum Labs) equipped with a 20 cm², 500 kD molecular weight cut off (MWCO) MicroKros® modified polyethersulfone (mPES) filter module (20) and the TFF pump (18) was set to 40 mL/min. The reagent delivery manifold dual head pump (36) was set to 40 mL/min. The duration of the PLL delivery step was set to 7.9 seconds or 5.3 mL (5.0 mL delivered +0.3 mL for dead volume). Off-line testing showed that actual deliveries to the particle reservoir (16) were accurate to +/−3%. Under these conditions HP deposition to an LBL film is independent of HP concentration in the range of 1.0-2.0 mg/mL, so this level of accuracy is sufficient for LBL steps. A model study was conducted where the TFF loop was charged with 20 mL suspension of 3% $CaCO_3$ microparticles. The TFF pump (18) was set to 40 mL/min and the suspension allowed to recirculate for 5 min. The particles were washed with permeation buffer (10 mM HEPES pH 7.0) by opening valves V5, V6, V7 (41, 44, 28) by computer control. The permeate volume was measured on a digital scale and the valves were closed by computer control when 100 g (100 mL) permeate was collected. Next, computer control opened valves V1, V2, V5 (35, 37, 44) for 7.9 seconds to deliver a 5.0 mL aliquot of 12.5 mg/mL PLL to the TFF loop. After five minutes permeate valve V7 (28) opened automatically to start a 120 second concentration step returning the TFF loop system volume back to 20 mL. Buffer inlet valves V5 and V6 (42, 44) were opened automatically to begin a permeation step and the suspension was washed with 100 mL (5×suspension volume) of buffer. Permeate samples (0.5 mL) were collected at 1 mL, 50 mL, and 100 mL permeation volume points for protein assay. When 100 g of permeate was collected by closing V5, V6, V7. A 0.5 mL sample of the final particle suspension was also collected, centrifuged, and the supernatant aspirated for protein assay.

Figure 2:
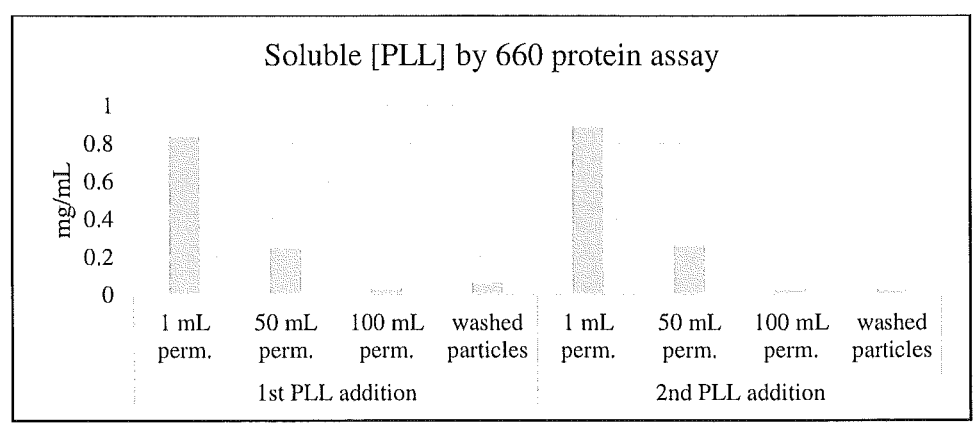
FIG. 2 is a graph showing exemplary TFF circulatory loop PLL concentrations during repetitive PLL addition followed by permeation cycles as measured by Pierce™ 660 nm Protein Assay.

Soluble PLL was measured by Pierce™ 660 nm Protein Assay, the results of which are shown in FIG. 2. Initial permeate [PLL] was about 0.85 mg/mL. After 50 mL permeation (2.5 suspension volumes) the soluble [PLL] decreased by approximately 65% and after 100 mL (5.0 suspension volumes) >95% had been removed. Repeat PLL delivery/permeation cycles gave similar results, demonstrating that the present computer controlled deliveries are reproducible and that excess HP removal is nearly complete after permeation for 5.0 suspension volumes.

An exemplary sample of the computer controlled steps used for a full cycle of LBL with PLL is shown in Table 1:

TABLE 1

Computer controlled operations for executing a single cycle of automated LBL by TFF

| Step | Running Time (sec) | Duration (sec) | Function | Instruction | User prompt initiated? |
|---|---|---|---|---|---|
| 1 | 0.0 | 8.0 | Add PLL | Open V1, V2, V5 | Yes |
| 2 | 8.0 | 0.1 | Stop PLL | Close V1, V2, V5 | No |
| 3 | 8.1 | 300.0 | Recirculation | | No |
| 4 | 308.1 | 120.0 | Concentrate | Open V7 | No |
| 5 | 428.1 | 272-1172 | Permeate | Open V5, V6 | No |
| 6 | 700-1600 | 0.1 | End Permeate @ 100 g collection | Close V5, V6, V7 | Yes |

With regard to Table 1, computer code results are expressed for control of valves for addition of a layer of PLL. A user prompt in the form of a mouse click at step 1 begins the sequence. A subsequent user prompt during step 6 after 100 g of permeate has been collected ends the step and the cycle. Because of variable and often diminishing TFF filter flux rates, the permeate time can vary from about 4 min to 20 min, or, for example 272 sec to 1172 sec. In exemplary embodiments, the computer can be configured to use feedback from the permeate collection vessel to initiate subsequent cycles when 100 g of permeate has been collected. For example, the collection vessel may rest upon a digital scale that has input and output connections to the computer. The computer instructs the scale to auto zero during step 1. When the scale output to the computer registers 100g, the computer executes step 6 automatically.

The above example demonstrates that computer controlled HP deliveries and subsequent permeation steps perform as desired and in a reliable fashion.

EXAMPLE 3

Semi-Automated Fabrication of a 7 HP Layer LBL Microparticle

A batch of $CaCO_3$ microparticles coated with a seven layer LBL film was prepared using the system and method described herein. The apparatus shown in FIG. 1 was used and operated as described in Example 2. Rounds of LBL by TFF were carried out with a user prompt in the form of a computer mouse click to start each round. The prompt is issued by the user when the permeate volume for that step reaches 100 mL, or 100 g as measured by a digital scale. As discussed above, the duration of each permeation step is variable so for exemplary purposes 571.9 sec permeation steps were used in Table 2. The details of the manufacturing process follow below.

Referring to FIG. 1, the TFF loop was equipped with a 20 cm², 500 kD (MWCO) MicroKros® mPES filter module (20). HP stock solutions of PGA sodium salt (5.0 mg/mL in 10 mM HEPES buffer Sigma-Aldrich cat. # P4636) and PLL-HBr salt (6.25 mg/mL in 10 mM HEPES buffer. Sigma-Aldrich cat. # P6516) were prepared and placed in 50 mL vials on the reagent delivery manifold at positions 32 and 34, respectively. The dual head pump (36) was set to 40 mL/min. Loops (38 and 40) were primed with HP solution by toggling valves V1-V4 open and closed under computer control with valve V5 (44) was open to waste. 20 mL of a 3% (wt/v) suspension of $CaCO_3$ microparticles (prepared as described in Example 1) was placed in the particle reservoir (16) and recirculated in the TFF loop at 40 mL/min. Stepwise automated LBL by TFF was performed by executing the steps displayed in Table 2. User prompts were issued by the operator at step 6 and step 12 at the point when 100 g of collected permeate was reached, as read from a digital scale. Steps 1-12 were performed three times to deposit six new HP layers to the microparticles, conferring seven HP layers total.

TABLE 2

Computer controlled operations for executing two cycles of automated LBL by TFF.

| Step | Running Time (sec) | Duration (sec) | Function | Instruction | User prompt initiated? |
|---|---|---|---|---|---|
| 1 | 0.0 | 8.0 | Add PLL | Open V1, V2, V5 | Yes |
| 2 | 8.0 | 0.1 | Stop PLL | Close V1, V2, V5 | No |
| 3 | 8.1 | 300.0 | Recirculation | | No |
| 4 | 308.1 | 120.0 | Concentrate | Open V7 | No |
| 5 | 428.1 | 300-1200 | Permeate | Open V5, V6 | No |
| 6 | 1000.0* | 0.1 | End Permeate @ 100 g collection | Close V5, V6, V7 | Yes |
| 7 | 1000.0 | 8.0 | Add PGA | Open V3, V4, V5 | No |
| 8 | 1008.0 | 0.1 | Stop PGA | Close V3, V4, V5 | No |
| 9 | 1008.1 | 300.0 | Recirculation | | No |
| 10 | 1308.1 | 120.0 | Concentrate | Open V7 | No |
| 11 | 1428.1 | 300-1200 | Permeate | Open V5, V6 | No |
| 12 | 2000* | 0.1 | End Permeate @ 100 g collection | Close V5, V6, V7 | Yes |

Particle samples were collected after each permeation step via syringe at the sample port (24) for zeta surface potential and film deposition measurements. Surface potentials were measured by DLS using a Zetasizer from Malvern Instruments and the results displayed in FIG. 3A show the expected alternating surface polarity pattern indicating successful LBL experiments. Stepwise LBL film deposition was measured by amino acid analysis performed on dried particle samples by the following procedure.

About 10 mg of LBL particles were dried under high vacuum and weighed. Particle samples were digested in 0.30 mL of 6.0 M HCl at 120° C. in sealed vials for 16 h. The HCl was evaporated under vacuum and the residue dissolved in borate buffer for amino acid derivitization with ortho-phthalaldehyde (OPA) using the methods and materials provided by Agilent Technologies. The amounts of each amino acid, in this case glutamate and lysine, were measured using a quantitative HPLC assay. The results in FIG. 3B show robust film growth, with steady accumulation of PLL and PGA at each LBL step, demonstrating that the semi-automated process works as desired. A bright field microscopy image of the particles in FIG. 3C shows that the 7 HP layer particle batch was well dispersed and lacked large aggregates.

Figure 3C:
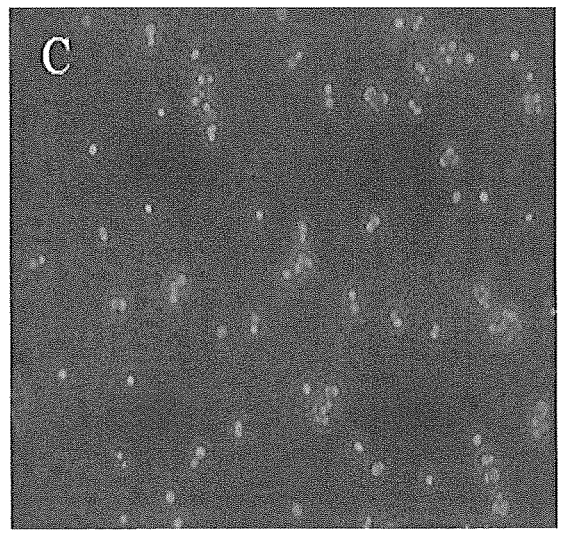
FIG. 3C shows dispersion of an exemplary 7 layer particle batch, wherein the layers are homopolypeptides.

With further reference to the examples illustrated by FIGS. 3A-3C, characterization of a 7 HP layer microparticle construct is shown by way of example, made by automated (semi-, in this case) LBL by TFF. With regard to FIG. 3A, stepwise zeta potential measurements show expected pattern of alternating polarity. FIG. 3B shows stepwise film deposition as measured by AAA indicating successful LBL by TFF, A microscopy image of the finished particles shown in FIG. 3C indicates that particles are well-dispersed with expected spherical morphology.

EXAMPLE 4

Semi-Automated Fabrication of an LBL Microparticle Vaccine Construct

With all data indicating that automated LBL by TFF was working well, a batch of a microparticle vaccine construct similar to those described previously in U.S. patent publication no. US20120009254 was prepared.

The apparatus and procedures used in Example 3 were repeated using a sterile 20 cm$^2$ 500 kD MWCO mPES TFF filter. Following the application of the seventh HP (PGA) layer and subsequent permeation step, a bolus of 12.5 mg DP in 5.0 mL buffer was added to the TFF loop via a syringe port (24 in FIG. 1). After 5 minutes of recirculation, the permeation valves V5, V6, and V7 (44, 42, 28 in FIG. 1) were opened by computer control, and the particles were washed with 100 mL buffer.

Figure 4A:
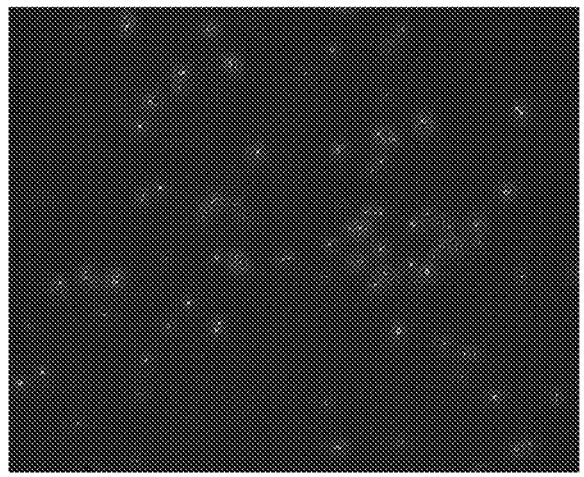
FIG. 4A shows microscopy image of 8 layer particles that are well dispersed.
Figure 4B:
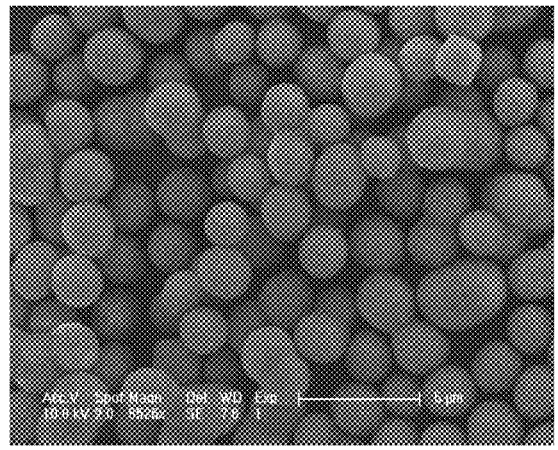
FIG. 4B shows an exemplary SEM image of 8 layer particles with 5.0 µm ruler inset.
Figure 4C:
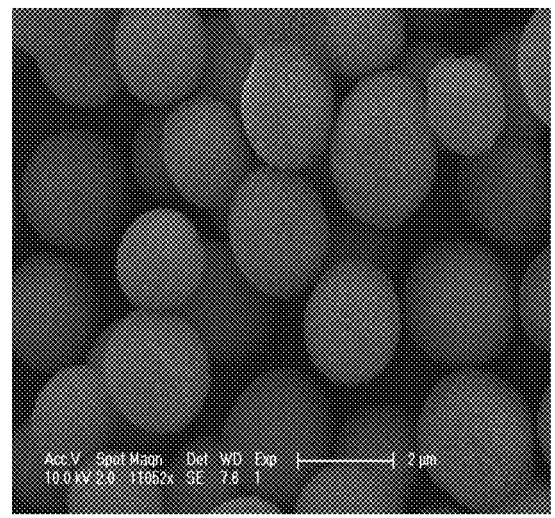
FIG. 4C shows another exemplary SEM image of 8 layer particles with 2.0 µm ruler inset.
Figure 4D:
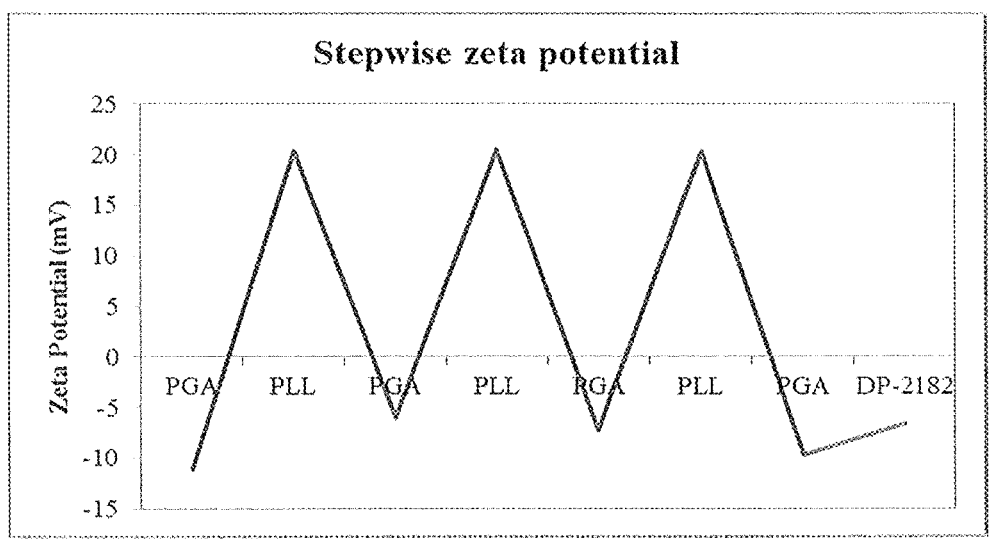
FIG. 4D shows stepwise zeta potential measurements collected on particles during the fabrication of an 8 layer LBL microparticle having an alternating polarity pattern seen for successful LBL experiments.
Figure 4E:
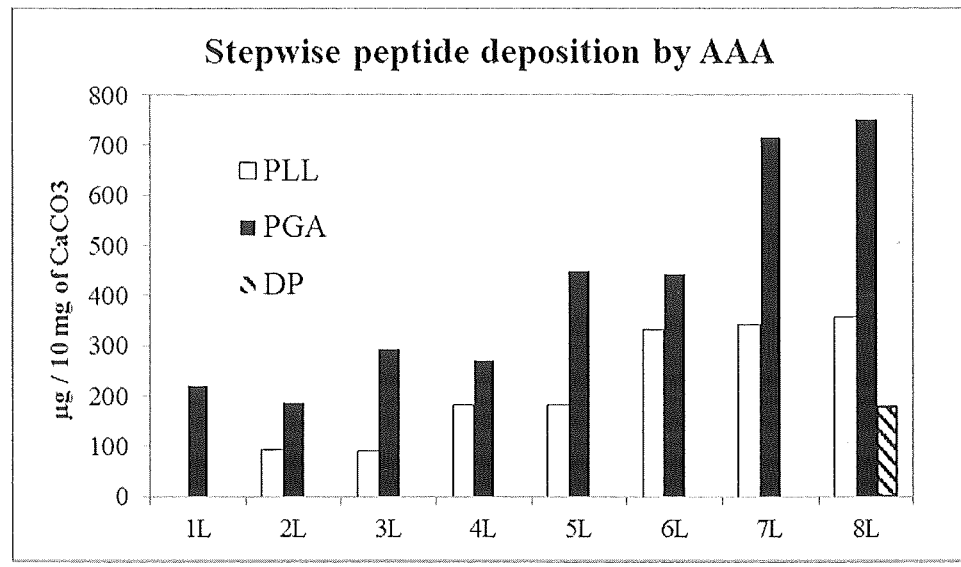
FIG. 4E shows exemplary stepwise LBL film deposition during the fabrication of an 8 layer LBL microparticle batch as measured by AAA.

The particles were characterized by microscopy (FIG. 4A) and scanning electron microscopy (SEM, FIG. 4B and 4C). As before, well-dispersed spherical porous particles were observed (see, e.g., FIG. 4A-C). Stepwise surface potential measurements performed on particle samples collected at the end of each permeation step exhibited alternating charge polarity indicative of successful LBL (FIG. 4D). Stepwise film deposition measured by AAA of samples collected after each LBL cycle showed steady accumulation of HPs in the LBL film (FIG. 4E). The AAA data collected from the final product determined that total DP adsorbed in this exemplary batch was 10.8 mg, indicating 86% recovery of DP in the film.

The efficiency of LBL film build up using the TFF method described here was compared to the efficiency of the manual centrifugation/aspiration/resuspension method. Two additional batches of this microparticle construct were prepared as described above and the total amount of HP and DP adsorbed to the film measured by AAA. Likewise, six batches of a similar construct were prepared using the manual method described in U.S. Publication no. 20120009254 and the total HP and DP adsorption measured by AAA. The average amounts of each component (PLL, PGA, and DP) were calculated as a function of µg peptide per mg dried CaCO$_3$ and are displayed graphically in FIG. 12. The results show that on average 2.5-3.5 fold more peptide was deposited by the automated LBL by TFF method.

A sterile TFF filter was used for this batch synthesis, but no other precautions were taken to prevent potential contamination by bacteria or other pathogens. Despite the lack of active measures to exclude bacteria from the system, endotoxin measurements performed on the final product by Pierce LAL Chromogenic Assay (Thermo Scientific) indicated 0.04 endotoxin units per µg of antigenic DP. This level is well within the acceptable range for immunizations of lab animals and strongly suggests that instituting simple precautions such as using sterilized buffers and good manufacturing practice (GMP) grade raw materials will decrease endotoxin to levels acceptable for human use.

EXAMPLE 5

Synthesis of LBL Microparticles with Protein Antigen Pigeon Cytochrome C

Figure 4F:
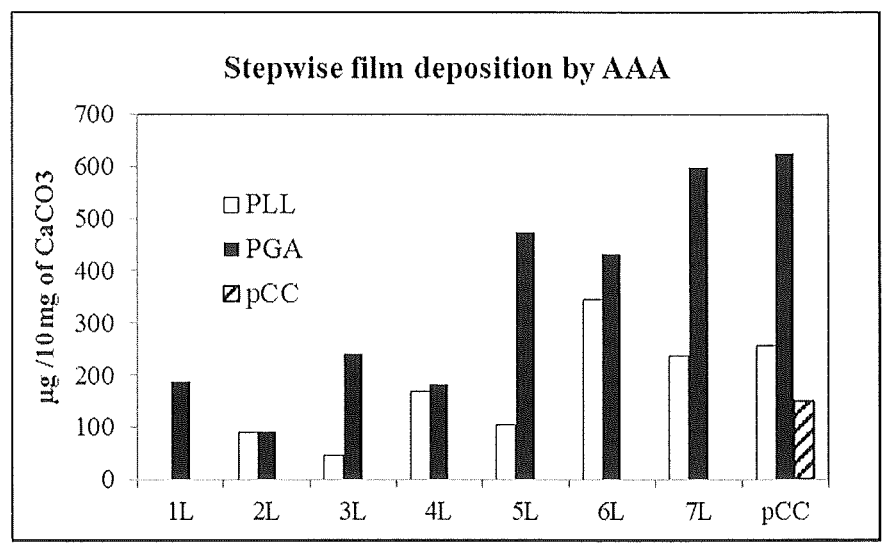
FIG. 4F shows another exemplary stepwise LBL film deposition during the fabrication of an 8 layer LBL microparticle batch as measured by AAA.

The apparatus in FIG. 1 and procedure used in Example 4 were used with following changes. First, the TFF loop was equipped with a 20 cm$^2$ 750 kD MWCO mPES TFF filter. Second, the final DP stock solution was replaced with 5.0 mL of a 2.5 mg/mL solution of pigeon cytochrome C (pCC, Sigma cat. # C4011) in 10 mM HEPES. This experiment was performed to demonstrate that whole native proteins can be incorporated efficiently into LBL films. No other changes of significance were made from Example 4. Samples of the particle suspension were collected after each permeation step and the LBL film quantitated by AAA. FIG. 4F shows steady accumulation of HPs after each LBL step as well as efficient incorporation of protein pCC. AAA determined that 8.1 mg (66%) of soluble pCC was captured in the film.

EXAMPLE 6

TFF Apparatus for Automated Synthesis of Sterile Vaccine Microparticles

Figure 5:
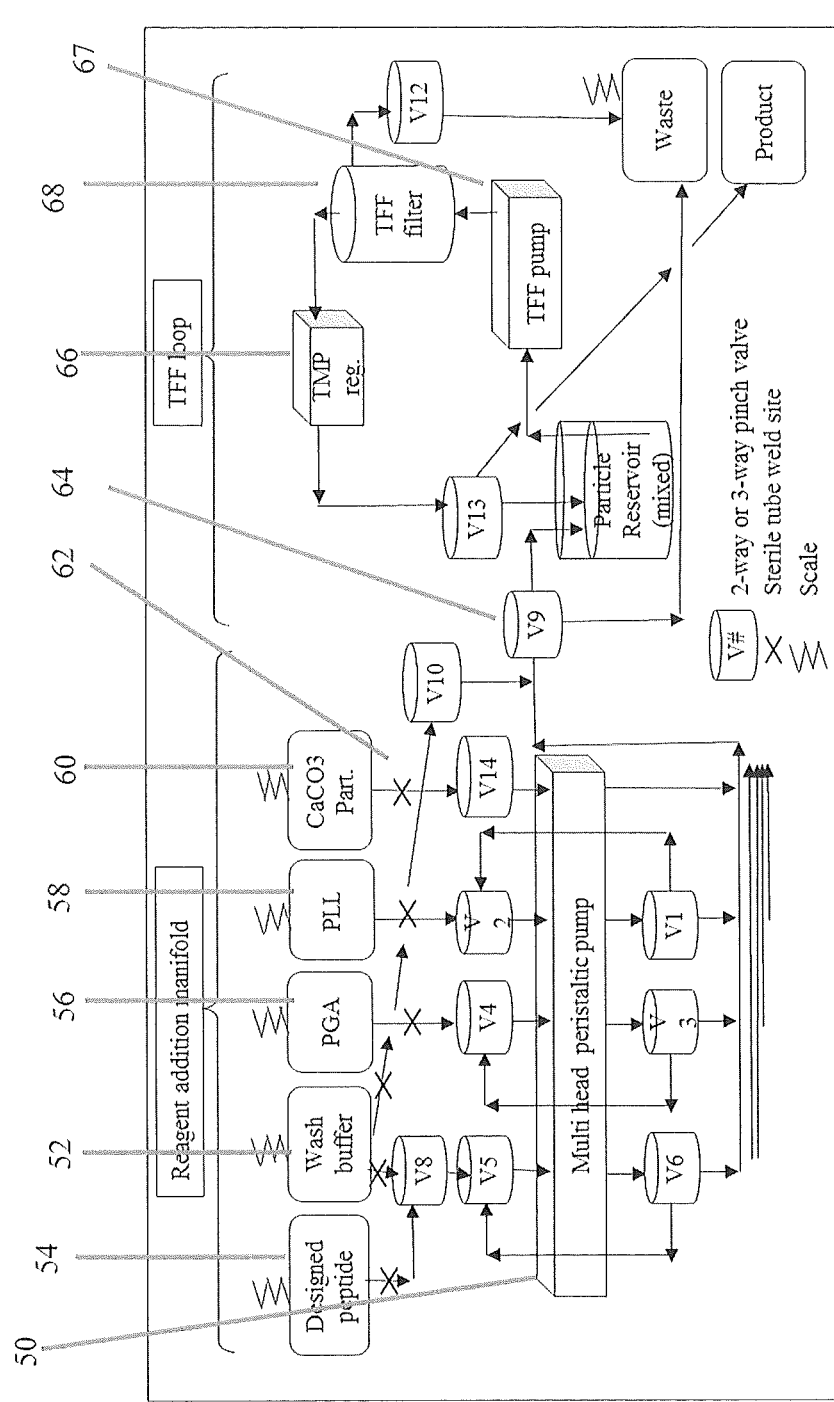
FIG. 5 shows another exemplary LBL by TFF system.

Referring to FIG. 5, several changes are made to the apparatus shown in FIG. 1. First, a four channel peristaltic pump replaces the dual head pump in the reagent addition manifold. This enables two more reagents, wash buffer (52) and DP (54) to be actively pumped and delivered to the TFF loop or flushed to the waste receptacle with washing buffer. Second, additional computer controlled valves are added to control when the reagents are delivered and the routes of delivery. Third, the reagent solutions are placed in plastic IV bags and suspended from scales. The scales are used to document that the correct reagent was withdrawn and in the correct amount at the appointed time. Records of the deliveries can be kept on validated computers or recorded manually on paper forms by attending technicians.

IV bags are chosen because they are readily available in sterilized form and come with supporting products that can execute sterile tube welds so that the reagents can be connected to the manifold without exposure to possible contamination. Provided that the tubing and TFF filter are sterile, and the soluble reagent solutions are sterile, and the starting CaCO$_3$ microparticles are sterile, and all the components are connected properly, then the end product will be sterile.

In one aspect, the tangential flow filtration loop comprises a sterile, closed-loop tubing network including a tangential flow filtration filter and a particle reservoir as shown in FIG. 1B. The closed-loop tubing network includes, for example, a TFF filter and a particle reservoir, wherein the network is assembled separately from the TFF pump. The tubing network with receiving bags and TFF filter are optionally intended to be single-use disposable materials. The closed-loop tubing network is optionally sterilized by treatment with gamma radiation, or ethylene oxide, or heat. In one aspect, the closed-loop tubing network is configured to be mounted to the TFF pump and at least one computer controlled valve, for example the permeate valve.

In certain aspects, the closed-loop tubing network extends to the soluble reagent addition manifold and mounts to at least one computer controlled valve for the purpose of dispensing a reagent to the tangential flow filtration loop. Optionally, the extended closed-loop tubing network is assembled separately from the reagent addition manifold, sterilized, and subsequently mounted to the TFF pump, TFF circulatory loop valves, and soluble reagent addition manifold valves.

The sterile closed-loop tubing network will be constructed of materials that are certified as compatible for the manufacture of biopharmaceuticals for human use. An example of a designed single use disposable network is shown in FIG. 6. Specified tubing, for example 1/16 inch inner diameter Tygon® tubing can be used. Tubing will be cut to specified lengths and joined with barbed polyethylene junctions. Clamps or cable 'zip' ties can be used to fasten all junctions to prevent leaks and ensure that a closed system is maintained. A sterile TFF filter (72), for example a 20 cm$^2$, 750 kD MWCO, mPES filter can be incorporated and all tube endings capped to exclude contaminants prior to sterilization. The complete unit can be packaged, wrapped, and submitted to an authorized and accredited facility for sterilization by, for example gamma irradiation, ethylene oxide treatment, or heat. The sterile shelf life of these units will need to be validated experimentally but lifetimes of >12 months are expected.

Prior to execution of an LBL particle batch synthesis, the network is unwrapped and mounted to all the various pinch valves and pump heads as shown in FIG. 5. Sterile stock solutions of, for example, PLL, PGA, washing buffer, designed polypeptide, and CaCO$_3$ microparticles in IV bags are prepared off-line. Sterilization of those reagents can be accomplished by filtration through 0.2 um filters, heating, or other techniques. The bags are spliced to the tubing network with a commercially available sterile tube-welding instrument.

Referring to FIG. 5, both the multi head peristaltic pump (50) and the TFF pump (67) are set to 40 mL/min and all scales are reset to 0.0 g. At that point all subsequent steps of the process can be executed remotely by computer control. No direct interaction with the device is required until it is time to collect the final product.

Table 3 provides an example of the steps that would be executed during the synthesis of a typical microparticle vaccine batch. As discussed above, an 8 layer construct is presented here for exemplary purposes but the process can be shortened or lengthened to prepare constructs with as few as 2 layers and as many as 50, or more. The level of interaction between the apparatus and the user will depend upon whether the apparatus is equipped with electronic feedback mechanisms as discussed above, or whether certain steps are initiated by a continue prompt from the user. There are no limitations to the amount of control that can be assigned to the computer but in practice it is desirable to have scheduled pauses between stages so that a user can certify and document that previous steps have been executed to specifications, and to collect samples for testing if desired.

TABLE 3

| Stage | User prompt initiated? | Function | Valves actuated | Duration (sec) [volume] | Pause (sec) | User action |
|---|---|---|---|---|---|---|
| Prime lines | Yes | prime buffer line | 5, 6 | 8.5 | 1.5 | |
| | No | | 5, 6 | 9.0 | 4.0 | |
| | No | prime PLL line | 1, 2 | 5.1 | 1.5 | |
| | No | | 1, 2 | 6.0 | 2.0 | |
| | No | wash line | 5, 6 | 5.0 | 4.0 | |
| | No | prime PGA line | 3, 4 | 4.0 | 1.5 | |
| | No | | 3, 4 | 5.0 | 2.0 | |
| | No | wash line | 5, 6 | 10 | 30 | Inspect lines |
| Load/wash particles | Yes | load CaCO3 | 14, 9 | 45 | 10 | |
| | No | rinse | 5, 6, 9 | 5.0 | 30 | record delivery |
| | No | wash | 5, 6 | 15 | | |
| | Yes | concentrate | 12 | [20 mL] | 30 | record volume |
| | Optional | permeate | 9, 10, 12 | [100 g] | | |
| LBL coating of particles | Yes | add PLL | 1, 2, 9 | 11.5 | | record delivery |
| | No | recirculate | | 300 | | |
| | No | permeate | 9, 10, 12 | [100 g] | | |
| | Optional | add PGA | 1, 2, 9 | 11.7 | | record delivery |
| | No | recirculate | | 300 | | |
| | No | permeate | 9, 10, 12 | [100 g] | | |
| | Optional | add PLL | 1, 2, 9 | 11.5 | | record delivery |
| | No | recirculate | | 300 | | |
| | No | permeate | 9, 10, 12 | [100 g] | | |
| | Optional | add PGA | 1, 2, 9 | 11.7 | | record delivery |
| | No | recirculate | | 300 | | |
| | No | permeate | 9, 10, 12 | [100 g] | | |
| | Optional | add PLL | 1, 2, 9 | 11.5 | | record delivery |
| | No | recirculate | | 300 | | |
| | No | permeate | 9, 10, 12 | [100 g] | | |
| | Optional | add PGA | 1, 2, 9 | 11.7 | | record delivery |
| | No | recirculate | | 300 | | |
| | No | permeate | 9, 10, 12 | [100 g] | | |
| | Optional | add DP | 5, 6, 8, 9 | 5.3 | | record delivery |
| | No | rinse | 5, 6, 9 | 2 | | |
| | No | recirculate | | 300 | | |
| | No | permeate | 9, 10, 12 | [100 g] | | |
| Collect product | Yes | empty TFF loop | 13 | 45 | | inspect lines |

Table 3: Computer issued instructions for execution of a microparticle vaccine batch.

EXAMPLE 7

Automated LBL by TFF System with Multiple Reagent Addition Manifold Pumps

Figure 10:
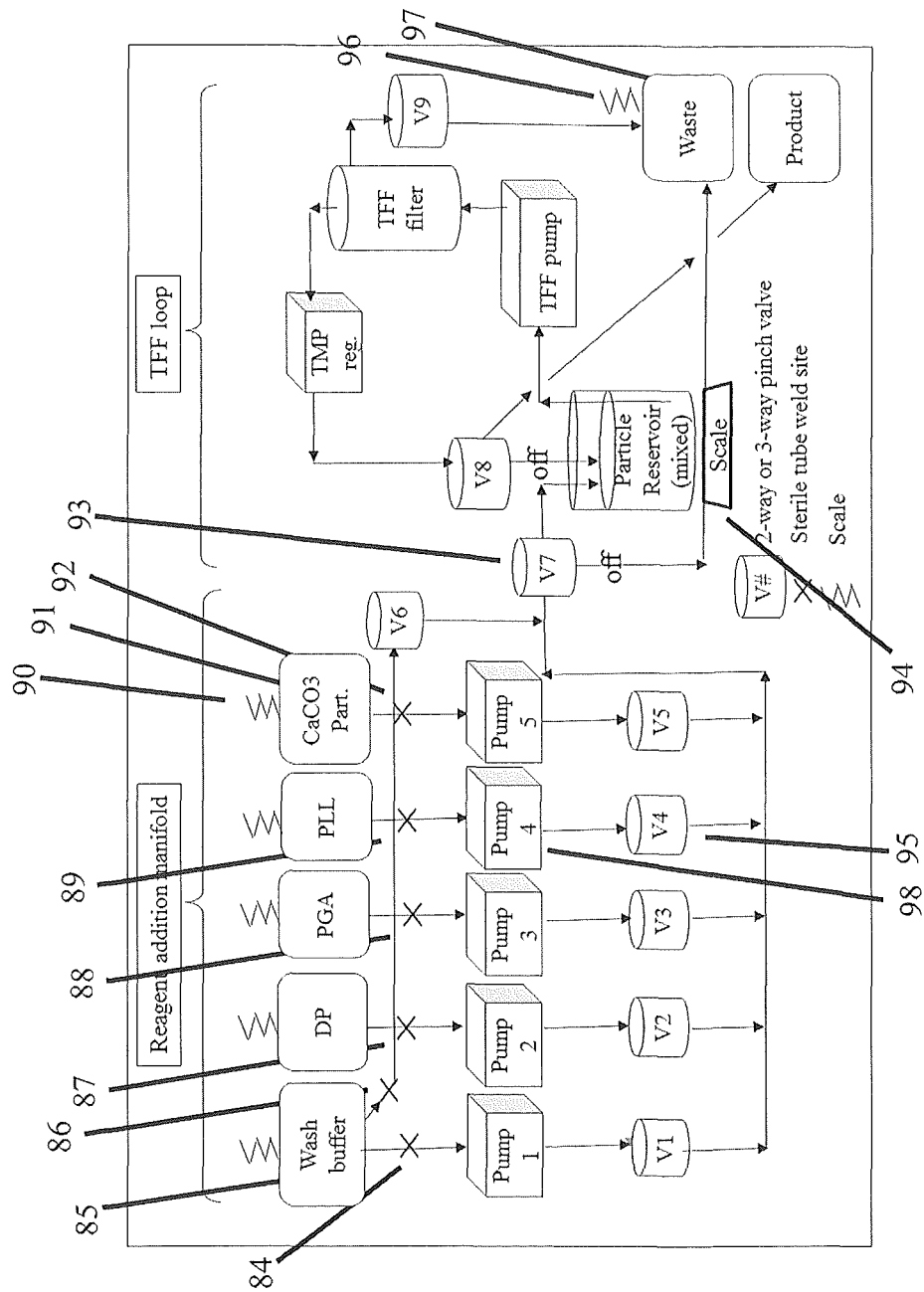
FIG. 10 is another exemplary LBL by TFF system that employs separate pumps to deliver each reagent to the TFF loop. The 'off' labels signify forward flow path when 3-way pinch valves are in off position.

The apparatus shown in FIG. 5 is reconfigured so that all of the pumped reagents are driven through separate peristaltic pumps as shown in FIG. 10. In this configuration, the pumps are individually controlled by the system computer. They remain at rest until instructed by the computer to deliver the desired reagent. The computer controls both the speed of the pumps and the duration of each delivery step. For example, in order to deliver 25 mL of PLL stock solution to the TFF loop, the computer opens valves V4 and V7 (95 and 93 in FIG. 10). It then instructs pump 4 (98 in FIG. 10) to pump at 40 mL/min for about 38 sec. The computer then stops pump 4 and closes V4 and V7. The computer then washes residual PLL solution to waste with wash buffer by opening V1 and turning on pump 1 at 40 mL/min for 15 sec. The computer also receives the output from an electronic scale (96) that the waste bag (97) hangs from. Since the flux rate of the TFF fiber filter varies, the length of each permeation step is defined by the weight of the volume of permeate collected, rather than a fixed time. An exemplary set of commands for the fabrication of a 100 mL scale batch of an 8 layer LBL microparticle construct is displayed in Table 4.

A sterile closed-loop system with a layout, for example as shown in FIG. 11 is mounted on the LBL by TFF apparatus shown in FIG. 10. The closed-loop system is equipped with a 300 mL particle reservoir, a 5 L waste bag, a 500 mL product bag, and a sterile 115 cm$^2$ 750 kD MWCO mPES TFF filter. A 200 mL batch of 1.5% suspension of CaCO$_3$ microparticles is prepared under sterile conditions and collected in a 300 mL sterile bag (91). The bag is then mounted to a scale (90) and sterile welded onto the system at tube weld site (92). Likewise, 4 L of 10 mM HEPES buffer pH 7.0 is prepared, sterile filtered through a 0.2 um membrane and collected in a 4 L sterile bag (85). The bag is hung from a scale and sterile welded at tube sites (84) and (86). 150 mL of PGA sodium salt stock solution at 5.0 mg/mL in HEPES buffer and 150 mg/mL of PLL HBr salt stock solution at 6.3 mg/mL in HEPES buffer are prepared, sterile filtered into sterile bags, mounted to hanging scales, and sterile tube welded to the apparatus at sites (88) and (89), respectively. Finally 40 mL of a 2.5 mg/mL solution of designed polypeptide (DP) in HEPES buffer is prepared, sterile filtered into a 100 mL sterile bag, mounted to a scale, and sterile welded at tubing site (87).

The TFF loop pump is set at 40 mL/min. The particle reservoir is mounted on a magnetic stir plate and set to stir at moderate speed. The user then prompts the computer to prime the lines on the reagent delivery manifold. After priming, the user inspects that lines to ensure proper priming then prompts the computer to deliver the CaCO$_3$ particles to the TFF loop. The user inspects the system to ensure proper delivery, then prompts the computer to start a concentration and washing cycle. The system is programed to terminate concentration at 100 g (mL) permeate collected and then to begin permeation for 400 g collected. The user inspects the TFF loop to ensure desired 100 mL (+/−10 mL) volume has been reached then prompts the computer to begin the repetitive LBL cycles. The deliveries of buffer, PGA, PLL, and DP are recorded by digital feedback to the computer and can be verified visually by the user. The user has the option to instruct the computer to continue automatically to the next LBL step or to pause for sample collection and documentation. After approximately 2.5 hours the final LBL microparticle suspension is delivered automatically to a 500 mL product bag. The tube to the product bag is sterile pinch welded and disconnected from the apparatus for analysis and formulation.

V6, V7, V8, and V9 are three way pinch valves that have one outlet open and one outlet closed when not powered on. While resting (not powered), V5 is closed to V7, V6 is closed to V8, V7 is closed to V5, V8 is closed to V6, and V9 is closed to the particle reservoir and open to the waste bag. Each valve is connected to its own individual channel on a relay board which in turn is connected to a computer. A power supply is also connected to the channels that the relay board uses to distribute power to actuate (open) the various valves. The computer contains the software that enables it to interface with the relay board and execute the sequence of steps shown in Table 5.

TABLE 4

| Stage | User prompt initiated.? | Function | Valves actuated | Duration (sec) or volume [g] | Pump @ 40 mL/min | Duration (sec) | User action |
|---|---|---|---|---|---|---|---|
| Prime lines | Yes | Gravity prime buffer line | 6 | [20] | | | Inspect lines |
| | No | prime buffer line | 1 | 15 | 1 | 12 | |
| | No | prime PLL line | 4 | 15 | 4 | 12 | |
| | No | wash line | 1 | 15 | 1 | 12 | |
| | No | prime PGA line | 3 | 15 | 3 | 12 | |
| | No | wash line | 1 | 15 | 1 | 12 | |
| | No | prime DP line | 2 | 10 | 2 | 6 | |
| | No | wash line | 1 | 20 | 1 | 17 | Inspect lines |
| Load/ wash particles | Yes | load 200 mL CaCO3 particles | 5, 7 | 310 | 5 | 305 | |
| | No | Rinse to reservoir | 1, 7 | 22 | 1 | 20 | record delivery |
| | Yes | concentrate | 9 | [100] | | | Verify, record loop volume |
| | No | permeate | 6, 9 | [400] | | | record volume |
| LBL coating of particles | Yes | add PLL | 4, 7 | 42 | 4 | 40 | record delivery |
| | No | wash line | 1 | 15 | 1 | 12 | |
| | No | recirculate | | 300 | | | |
| | No | permeate | 6, 9 | [400] | | | |
| | No | add PGA | 3, 7 | 42 | 2 | 40 | record delivery |
| | No | wash line | 1 | 15 | 1 | 12 | |
| | No | recirculate | | 300 | | | |
| | No | permeate | 6, 9 | [400] | | | |
| | No | add PLL | 4, 7 | 42 | 4 | 40 | record delivery |
| | No | wash line | 1 | 15 | 1 | 12 | |
| | No | recirculate | | 300 | | | |
| | No | permeate | 6, 9 | [400] | | | |
| | No | add PGA | 3, 7 | 42 | 3 | 40 | record delivery |
| | No | wash line | 1 | 15 | 1 | 12 | |
| | No | permeate | 6, 9 | [400] | | | |
| | No | add PLL | 4, 7 | 42 | 4 | 40 | record delivery |
| | No | wash line | 1 | 15 | 1 | 12 | |
| | No | recirculate | | 300 | | | |
| | No | permeate | 6, 9 | [400] | | | |
| | No | add PGA | 3, 7 | 42 | 3 | 40 | record delivery |
| | No | wash line | 1 | 15 | 1 | 12 | |
| | No | recirculate | | 300 | | | |
| | No | permeate | 6, 9 | [400] | | | |
| | No | add DP | 2, 7 | 42 | 2 | 40 | record delivery |
| | No | rinse to reserv. | 1, 7 | 8 | 1 | 5 | |
| | No | recirculate | | 300 | | | |
| | No | permeate | 6, 9 | [400] | | | |
| Collect product | No | empty TFF loop | 8 | 160 | | | Inspect, seal product bag |

EXAMPLE 8

Figure 13:
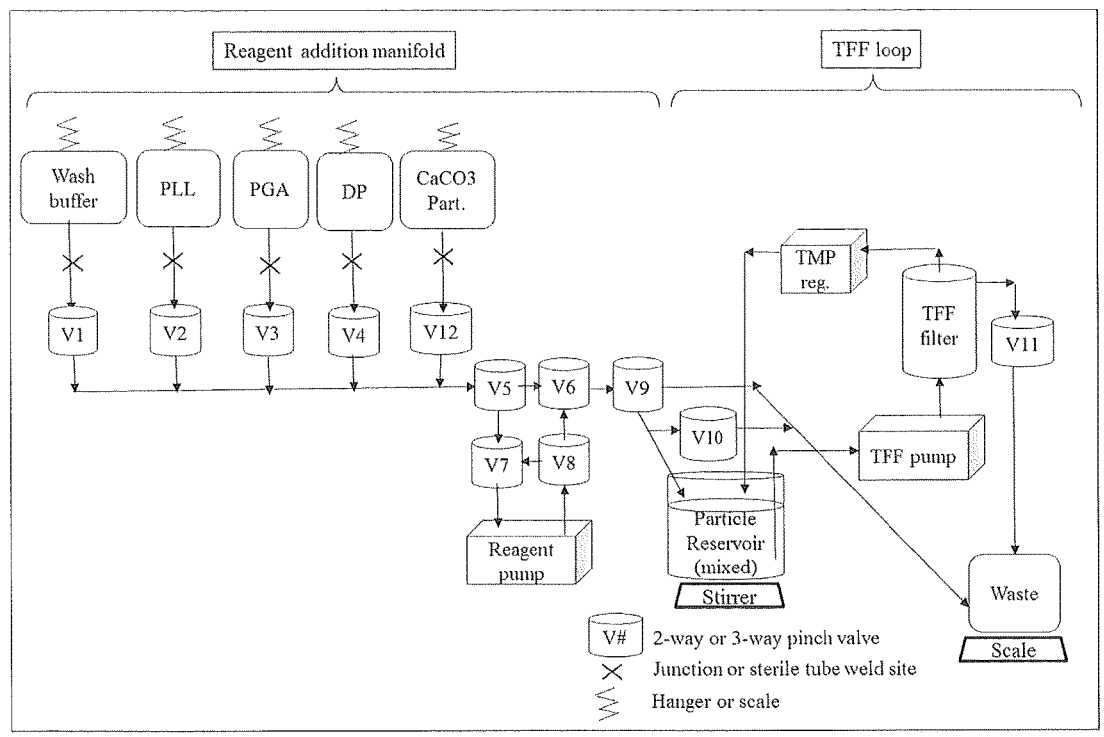
FIG. 13 is another exemplary LBL by TFF system that was used to make a batch of 7 homopolymer layer LBL microparticles at 100 mL scale (computer not included in figure)
Figure 14:
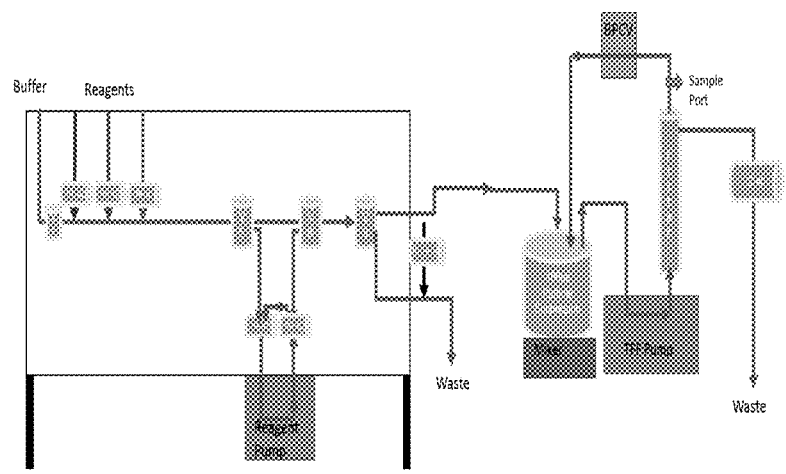
FIG. 14 is a photograph of actual LBL by TFF system used to make batch of 7 homopolymer layer LBL microparticles at 100 mL scale (computer not included in figure). Soluble reagent bags shown.

TFF Apparatus for Automated Synthesis of Sterile Vaccine Microparticles at 100 mL Batch Scale The apparatus shown in FIG. 5 was redesigned to a more streamlined system shown schematically in FIG. 13 and photographically in FIG. 14. Electrically activated solenoid pinch valves compatible with 1/8 inch ID and 1/4 inch OD tubing were mounted to a peg board in the arrangement shown. Valves V1, V2, V3, V4, V10, V11, and V12 are normally closed two-way solenoid pinch valves. Valves V5, A tubing network essentially the same at that shown schematically in FIG. 15 was assembled from 1/8 ID 1/4 OD silicone tubing, polypropylene barbed junctions and tees, a screw top 250 mL particle reservoir vessel equipped with three ports and a stir bar, and a 115 cm$^2$, 750 kD MW cutoff modified polyethersulfone (PES) TFF column (Spectrum Labs), and a 5 L waste bag. The tubing lengths were set so as to keep dead volumes to a practical minimum. The soluble reagent junction positions are capped or closed with clamps. The network can be used as is, or if aseptic processing is required can be packaged and sterilized by treatment with gamma radiation at a suitable facility. Tubing segments can be optionally labeled to clarify which valve or pump that segment is to be mounted to.

The assembled network is mounted to the various pinch valves, two peristaltic pumps, and clamps for the securing the particle reservoir vessel on a stir plate and the TFF column. The TFF column is equipped with ports for attaching pressure transducers so that the pressure gradient across the TFF membrane can be monitored. The transducer outputs are recorded by the computer and displayed continuously on the monitor. The waste bag is placed on a digital scale. The scale's output is recorded by the computer and is used to measure when sufficient permeation volumes have been collected.

Custom software was written to execute the steps in Table 5. The software actuates (opens) specific pinch valves in the sequence shown in the table. Steps that require a fixed volume delivery are time constrained and are denoted in the duration column in seconds (sec). Steps that require a certain volume of buffer to exit the system via permeate valve V11 are mass constrained and are denoted in grams (g). As aqueous permeate has a density of 1.0 g/mL its mass in grams essentially equals its volume in milliliters. At the beginning of a volume constrained step the computer reads the digital output from the waste bag scale and monitors it until it increases by the specified amount. For example, during a particle washing step that calls for 500 mL of permeation buffer to enter and exit the TFF loop, the computer will monitor the scale until the mass of the waste bag increases by 500 g and then progress to the next step in the table.

The custom software allows for the synthesis to be run in either fully automatic mode from start to finish and without user intervention, or in semi-automatic mode where at the end of each stage the system pauses and a notification in the form of an alarm or an email is sent to the user informing him/her that the stage is complete and the system is waiting for a continue prompt. In this mode, the user can step away from the device and not miss an opportunity to take a sample or inspect components for proper operation.

Valve V10 in FIG. 13 and its corresponding tubing segment were added as a vent allowing surplus air pressure in the particle reservoir to be vented to waste. The vent is normally closed and is only opened during the column washing and particle addition/concentration steps.

EXAMPLE 9

Semi-Automated Fabrication of a 7 HP layer LBL Microparticle by TFF at 100 mL Scale The LBL by TFF apparatus described in Example 8 and shown in FIG. 13 was used. Stock solutions of 10 mM HEPES buffer pH 7 (5 L), PGA in HEPES buffer (100 mL, 5.0 mg/mL), PLL in HEPES buffer (125 mL, 6.25 mg/mL), and 1.6% $CaCO_3$ microparticle suspension in PGA saline prepared by the method in Example 1 (200 mL) were placed in appropriate sized bags and attached to the tubing upstream of valves V1, V2, V3, and V12 respectively by barbed tubing connections. The soluble reagent bags were hung above the valves so as to promote gravity feed of reagents as shown in FIG. 14. The particle suspension bag was left inverted so as to prevent particle settling and particle dam formation at the tubing port(s). For aseptic runs, the HEPES, PGA, and PLL solutions are first sterilized by filtration through a 0.2 um filter and attached the network using a sterile tube welder.

The reagent delivery peristaltic pump was set to run at 120 mL/min, the TFF loop peristaltic pump was set to run at 100 mL/min, and the stir plate under the particle reservoir was set to medium speed. The software that executes the steps outlined in Table 5 was set to semi-manual mode meaning that at the end of each stage the computer will send a notification email to the user and pause at that step until prompted by the user to continue.

The priming and column washing stages in Table 5 were executed. The reagent bag containing the 1.6% particle suspension was gently inverted several times to disperse settled particles, hung in the upright position, and the particle loading and concentration routine in Table 5 was executed. Following these steps, the TFF loop contained approximately 100 mL of approximately 3% particle suspension. A particle sample (approximately 0.3 mL) was collected manually via an in-line syringe port that was placed in the TFF loop.

Figure 16A:
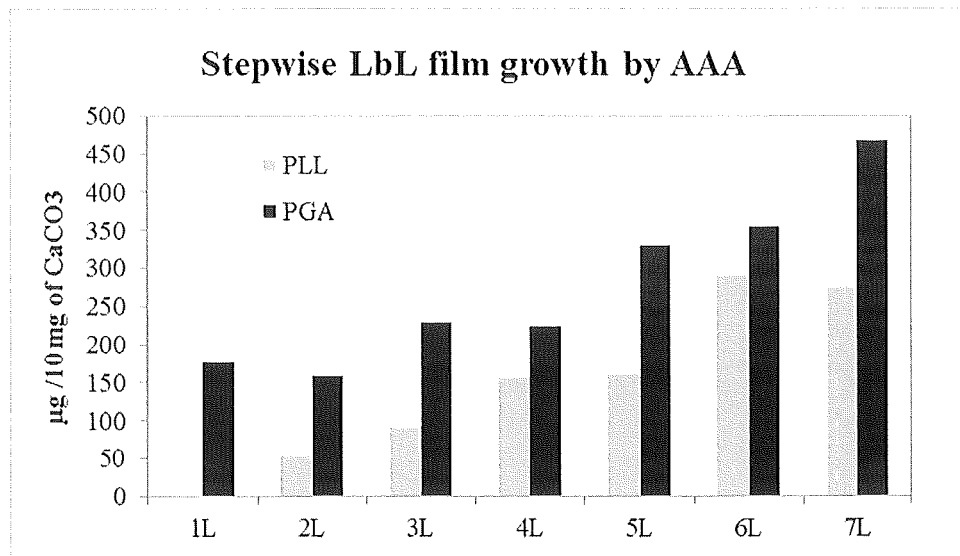
FIG. 16A shows exemplary stepwise LBL film deposition during the fabrication of a 7 layer LBL microparticle batch made on 100 mL scale as measured by AAA.
Figure 16B:
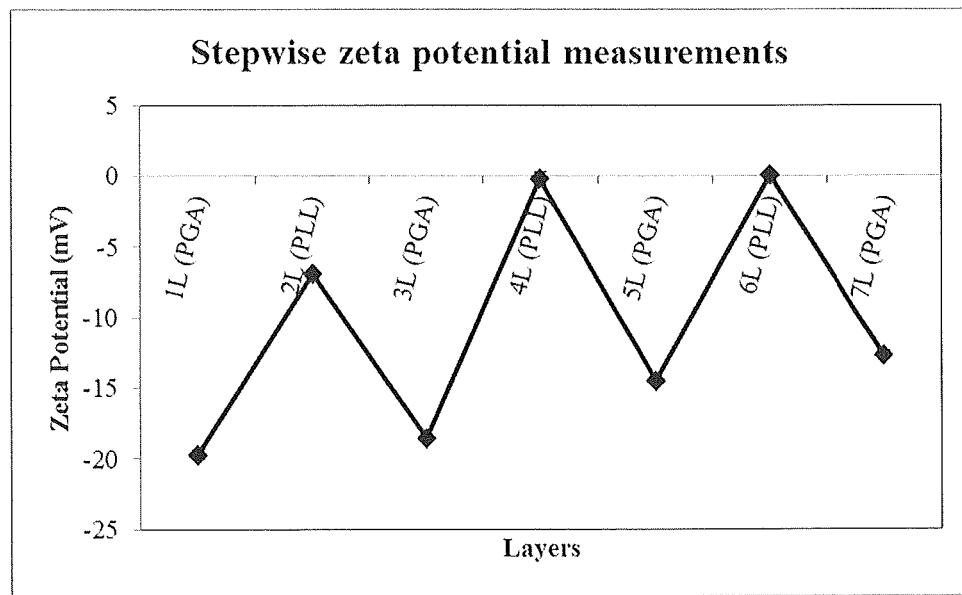
FIG. 16B shows exemplary stepwise zeta potential data measured on samples collected during the fabrication of a 7 layer LBL microparticle batch made on 100 mL scale

The PLL deposition step in Table 5 was started and a total of six rounds of automated LBL were performed, each ending with a pause and sample collection. Particle samples were dried under high vacuum in tared glass digestion vessels and subjected to the AAA procedure described in Example 3. The AAA data in FIG. 16A show steady accumulation of homopolymers PLL and PGA and a robust LBL film. Additionally, zeta surface potential measurements were performed on a Malvern Instruments Zetasizer and the data shown in FIG. 16B show the expected change of about 15 mV in either the positive direction following a PLL deposition step or negative direction following a PGA deposition step. Examination of the particles by microscopy showed they were well dispersed and spherical shape.

This particular synthesis was stopped at 7 layers. Addition of 25 mL of a 2.5 mg/mL designed peptide solution followed by the steps shown in the final stage of Table 5 would result in the vaccine microparticle drug substance as described in Example 4.

TABLE 5

| Stage | Function | Valves | Status | Delay time (sec) or permeate collected (g) | Target TFF loop volume (mL) |
|---|---|---|---|---|---|
| Priming | Prime buffer line | 1, 5, 6, 7, 8 | On | 8.0 sec | |
| | | 1, 5, 6, 7, 8 | Off | 1.5 sec | |
| | | 1, 5, 6, 7, 8 | On | 5.0 sec | |
| | | 1, 5, 6, 7, 8 | Off | 4.0 sec | |
| | Prime PLL line | 2, 5, 6, 7, 8 | On | 1.0 sec | |
| | | 2 | Off | | |
| | | 1 | On | 8.0 sec | |
| | | 1, 5, 6, 7, 8 | Off | 4.0 sec | |

TABLE 5-continued

| Stage | Function | Valves | Status | Delay time (sec) or permeate collected (g) | Target TFF loop volume (mL) |
|---|---|---|---|---|---|
| | Prime PGA line | 3, 5, 6, 7, 8 | On | 1.0 sec | |
| | | 3 | Off | | |
| | | 1 | On | 8.0 sec | |
| | | 1, 5, 6, 7, 8 | Off | 5.0 sec | |
| | Buffer to waste | 1 | On | 10.0 sec | |
| | | 1 | Off | | |
| Wash TFF column | Deliver 75 mL buffer | 1, 5, 6, 7, 8, 9 | On | 30 sec | 75 |
| | | 11 | On | 10 sec | |
| | Concentrate | 1, 5, 6, 7, 8, 9 | Off | 50 g | |
| | | 11 | Off | 5.0 sec | 25 |
| | Vent reservoir | 10 | On | 8.0 sec | 25 |
| | | 10 | Off | 5.0 sec | 25 |
| | permeate | 1, 9, 11 | On | 300 g | 25 |
| | | 1, 9, 11 | Off | 5.0 sec | 25 |
| | Add 60 mL buffer | 1, 5, 6, 7, 8, 9 | On | 32.7 sec | 85 |
| | | 1, 5, 6, 7, 8, 9 | Off | 5.0 sec | 85 |
| | Vent reservoir | 10 | On | 8.0 sec | 85 |
| | | 10 | Off | 5.0 sec | 85 |
| | Add 10 mL buffer | 1, 5, 6, 7, 8, 9 | On | 7.0 sec | 95 |
| | | 1, 5, 6, 7, 8, 9 | Off | 5.0 sec | 95 |
| | Vent reservoir | 10 | On | 8.0 sec | 95 |
| | | 10 | Off | 5.0 sec | 95 |
| | permeation | 1, 9, 11 | On | 20 sec | 95 |
| | | 1, 9, 11 | Off | | 95 |
| | Email and/or pause | | | | |
| Add particles to reservoir | Deliver 25 mL particles | 12, 5, 6, 7, 8 | On | 4.8 sec | 95-110 |
| | | 9, 11 | On | 7.8 sec | 110-130 |
| | | 12 | Off | | 110-130 |
| | Flush to reservoir | 1 | On | 7.4 sec | 110-130 |
| | Concentrate | 1, 5, 6, 7, 8, 9 | Off | >15 g | 110-130 |
| | Repeat previous 5 steps 8x | | | | 110-130 |
| | Concentrate | | | 280 g (from start of particle delivery) | 95 |
| | | 11 | Off | | 95 |
| | Washing | 1, 9 | On | 200 g | 95 |
| | | 1, 9 | Off | | 95 |
| | Email and/or pause | | | | |
| PLL deposition | Add 25 mL PLL | 2, 5, 6, 7, 8 | On | 5.9 sec | 95 |
| | | 9 | On | 6.6 sec | |
| | | 2 | Off | | |
| | | 1 | On | 8.6 sec | |
| | Recirculate | 1, 5, 6, 7, 8, 9 | Off | 300 sec | 125 |
| | Concentrate | 11 | On | 30 g | 95 |
| | Permeate | 1, 9 | On | 500 g | 95 |
| | | 1, 9, 11 | Off | | 95 |
| | Manual sampling | | Wait | 20 sec | 95 |
| | Email and/or pause | | | | |
| PGA deposition | Add 25 mL PGA | 3, 5, 6, 7, 8 | On | 5.5 sec | 95 |
| | | 9 | On | 7.0 sec | |
| | | 3 | Off | | |
| | | 1 | On | 6.2 sec | |
| | Recirculate | 1, 5, 6, 7, 8, 9 | Off | 300 sec | 125 |
| | Concentrate | 11 | On | 30 g | 95 |
| | Permeate | 1, 9 | On | 500 g | 95 |
| | | 1, 9, 11 | Off | | 95 |
| | Manual sampling | | Wait | 20 sec | 95 |
| | Email and/or pause | | | | |
| PLL deposition | Repeat above cycles | | | | 95 |
| PGA deposition | Repeat above cycles | | | | 95 |
| PLL deposition | Repeat above cycles | | | | 95 |
| PGA deposition | Repeat above cycles | | | | 95 |

TABLE 5-continued

| Stage | Function | Valves | Status | Delay time (sec) or permeate collected (g) | Target TFF loop volume (mL) |
|---|---|---|---|---|---|
| Designed Peptide Deposition | Deliver 25 mL DP solution | 4, 5, 6, 7, 8 | On | 5.1 sec | 95 |
| | | 9 | On | 7.4 sec | |
| | | 4 | Off | | |
| | | 1 | On | 7.8 sec | 125 |
| | Recirculate | 1, 5, 6, 7, 8, 9 | Off | 300 sec | 125 |
| | Concentrate | 11 | On | 30 g | 95 |
| | Permeate | 1, 9 | On | 500 g | 95 |
| | | 1, 9, 11 | Off | | 95 |
| | Manual sampling Email and/or pause | | Wait | 20 sec | 95 |

The examples described herein demonstrate that excellent vaccine microparticles can be prepared using automated or semi-automated LBL by TFF.

Additional contemplated aspects include assembly and mounting of parts (pinch valves, wires, etc.) on a fixed vertical platform to provide additional aspects to be added without entanglements.

Another exemplary schematic of an automated system is illustrated at FIG. 5. This exemplary embodiment provides a 4-channel peristaltic pump 50 to deliver washing buffer 52 and designed polypeptide 54 in addition to the HPs (see PGA 56, PLL 58, CaCO$_3$ suspension 60 in FIG. 5). Soluble reagent bags can be sterile welded (see 62 in FIG. 5) to the manifold and hang form digital scales that will record the time and quantity of the deliveries. Computer controlled valves, e.g., 2-way or 3-way pinch valves, are illustrated at 64. An exemplary TFF loop is illustrated generally at 66. In exemplary embodiments, the designed peptide may not require careful metering, as it is likely that all of that reagent would be delivered in a single bolus.

In exemplary embodiments, sterile reagents in bags are attached to a closed system by sterile tube welding (X). CaCO$_3$ particle suspension is delivered to the reservoir vessel by gravity, where it is gently mixed by mechanical stirring. Particles circulate through the filter loop continuously during processing. Concentrated HP stock solutions, designed peptide, and wash buffer are introduced to the reservoir in controlled amounts and at preset times via computer controlled pinch valves. Scales record changes in weight to confirm correct deliveries. Excess soluble reagents from LBL steps are eliminated tangentially from the TFF filter to waste. Following the final wash step the vaccine particle suspension is delivered to a product bag for off-line release testing and formulation.

A schematic for an exemplary closed-loop tubing network that would fit into this design in shown in FIG. 6. This embodiment includes fixed length tubing segments 68, barbed junctions 70, a TFF filter column 72, a reservoir 74 with stir bar 76 of other internal mixing device, and receiving bags for waste 78 and product 80. Labeling could be included at each junction to ensure proper mounting onto the device and correct welding of reagents. In exemplary embodiments, the closed loop consists entirely of tubing, barbed junctions, the TFF filter column, the enclosed particle reservoir with stir bar, and receiving bags for waste and product.

A schematic for an exemplary closed-loop tubing network that would fit into a reagent delivery manifold configured with separate pumps for each reagent is shown in FIG. 11.

Figure 7:
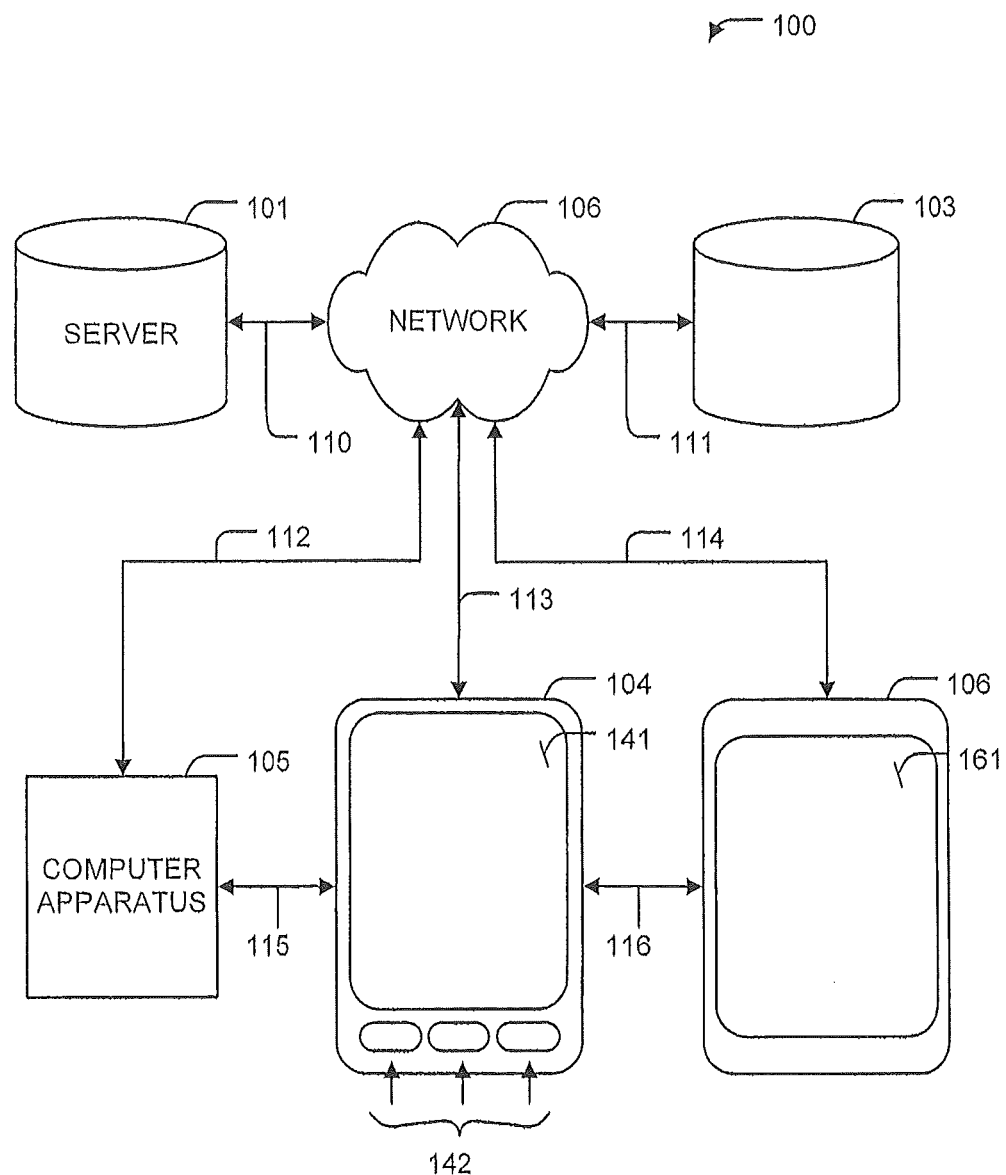
FIG. 7 is an illustration of an exemplary system diagram in accordance with exemplary embodiments of the invention.

This embodiment includes all of the components in the network shown in FIG. 6 and includes sites for sterile welding of sterile reagents to the manifold (84, 86, 87, 88, 89, 92 in FIG. 11.) As explained previously, the closed loop can be assembled under GMP conditions, packaged, sterilized, and then stored until use FIG. 7 illustrates an exemplary system for automated LBL by TFF. The system 100 may include a server 101 (or simply a local computer). The server 101 may include a plurality of information, including but not limited to, information and profiles, algorithms and processing modules and other data storage. The server 101 may be in communication with a network 106 via a communication channel 110.

Additionally, the system 100 may access or interface with additional, third party data sources or servers 103. Third party sources of data 103 may be in communication with the network 106 via a communication channel 111. It is noted that although illustrated as separate, the source 103 may include a server substantially similar to server 101. The server 101 or source 103 may include a data service provider, for example, a cellular service provider, a business information provider, or any other suitable provider or repository. The server 101 or source 103 may also include an application server providing applications and/or computer executable code implementing any of the interfaces/methodologies described herein. The server 101 or source 103 may present a plurality of application defaults, choices, set-ups, and/or configurations such that a device may receive and process the application accordingly. The server 101 or source 103 may present any application on a viewer interface or web-browser of a device for relatively easy selection by a viewer of the device. The viewer interface or web page rendered for application selection may be in the form of an application store and/or application marketplace.

Alternately, another server component or local computer apparatus, e.g., 104, 105 and/or 106, may produce the viewer interface and control connectivity to the server 101 or source 103. Also, the server 101 or one or more of the local computer apparatus 104, 105 and 106 may be configured to periodically access the source 103 and cache data relevant to data used in embodiments of the present invention.

The network 106 may be any suitable network, including the Internet, wide area network, and/or a local network. The server 101 and the source 103 may be in communication with the network 106 over communication channels 110, 111. The communication channels 110, 111 may be any suitable communication channels including wireless, satellite, wired, or otherwise.

An exemplary system 100 further includes computer apparatus 105 in communication with the network 106, over communication channel 112. The computer apparatus 105 may be any suitable computer apparatus including a personal computer (fixed location), a laptop or portable computer, a personal digital assistant, a cellular telephone, a portable tablet computer, a portable audio player, or otherwise. For example, the system 100 may include computer apparatuses 104 and 106, which are embodied as a portable cellular telephone and a tablet, respectively. The apparatuses 104 and 106 may include display means 141, 161, and/or buttons/controls 142. The controls 142 may operate independently or in combination with any of the controls noted above.

Further, the apparatuses 104, 105, and 106 may be in communication with each other over communication channels 115, 116 (for example, wired, wireless, Bluetooth channels, etc.); and may further be in communication with the network 106 over communication channels 112, 113, and 114.

Therefore, the apparatuses 104, 105, and 106 may all be in communication with one or both of the server 101 and the source 103, as well as each other. Each of the apparatuses may be in severable communication with the network 106 and each other, such that the apparatuses 104, 105, and 106 may be operated without constant communication with the network 106 (e.g., using data connection controls of an interface). For example, if there is no data availability or if a viewer directs an apparatus to work offline, e.g., without immediate network connection, the data used by any of the apparatuses 104, 105, and 106 may be based on stored or cached information/parameters. It follows that each of the apparatuses 104, 105, and 106 may be configured to perform the methodologies described in the various exemplary embodiments.

Furthermore, using any of the illustrated communication mediums, the apparatuses 104, 105, and 106 may manipulate, share, transmit, and/or receive different data previously or currently produced at any one of the illustrated elements of the system 100. For example, data may be available on the server 101 and/or the source 103. Moreover, viewers of any of the devices 104, 105, and 106 may independently manipulate, transmit, etc., data, e.g., to separately determine a current value of the index at a given time.

Additionally and as described above, example embodiments of the invention may be embodied in the form of computer-implemented processes and apparatuses for practicing those processes (e.g., software controlling the LBL by TFF). Therefore, according to an example embodiment, the methodologies described hereinbefore may be implemented by a computer system or apparatus. A computer system or apparatus may be somewhat similar to the mobile devices and computer apparatuses described above, which may include elements as described below.

Figure 8:
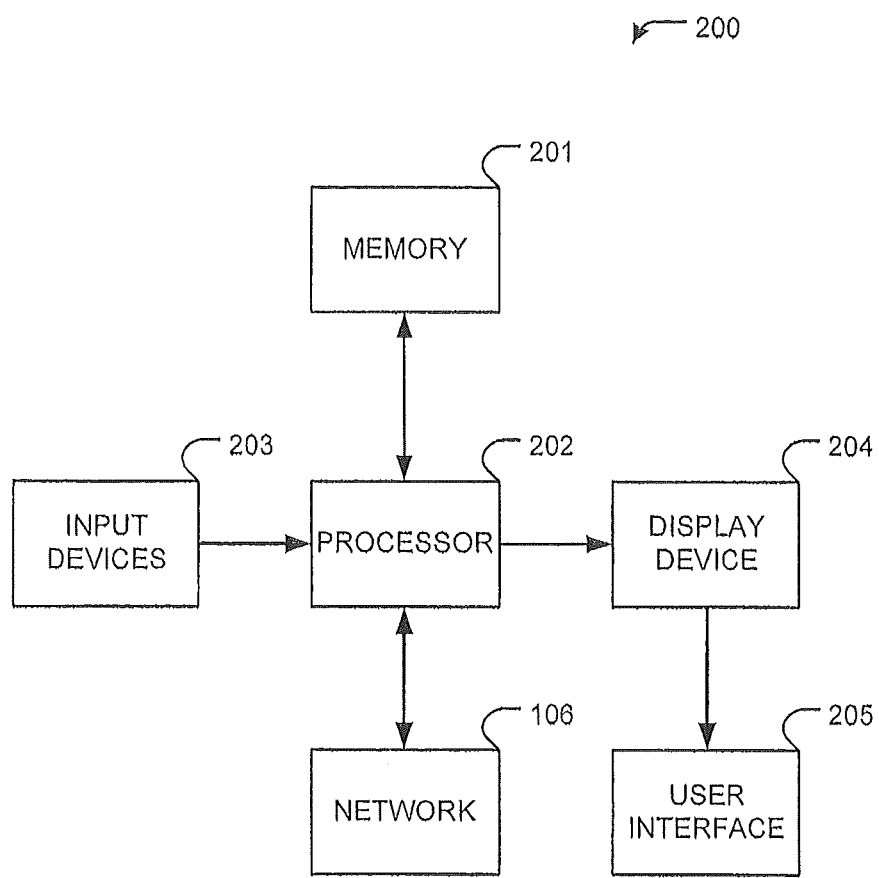
FIG. 8 is an exemplary computer system diagram.

FIG. 8 illustrates a computer apparatus, according to an exemplary embodiment. Portions or the entirety of the methodologies described herein may be executed as instructions in a processor 202 of the computer system 200. The computer system 200 includes memory 201 for storage of instructions and information, input device(s) 203 for computer communication, and display device 204, which may display a user interface 205. The user interface can provide a user with prompts for action, such as providing an indication of the need for a manual user click to initiate a polyelectrolyte deposition cycle. The computer system 200 may further be connected to the network 206. Alternatively, computer control includes a user interface configured to display the status of at least one polyelectrolyte deposition cycle.

Thus, the present invention may be implemented, in software, for example, as any suitable computer program on a computer system somewhat similar to computer system 200. For example, a program in accordance with the present invention may be a computer program product causing a computer to execute the example methods described herein.

Figure 9:
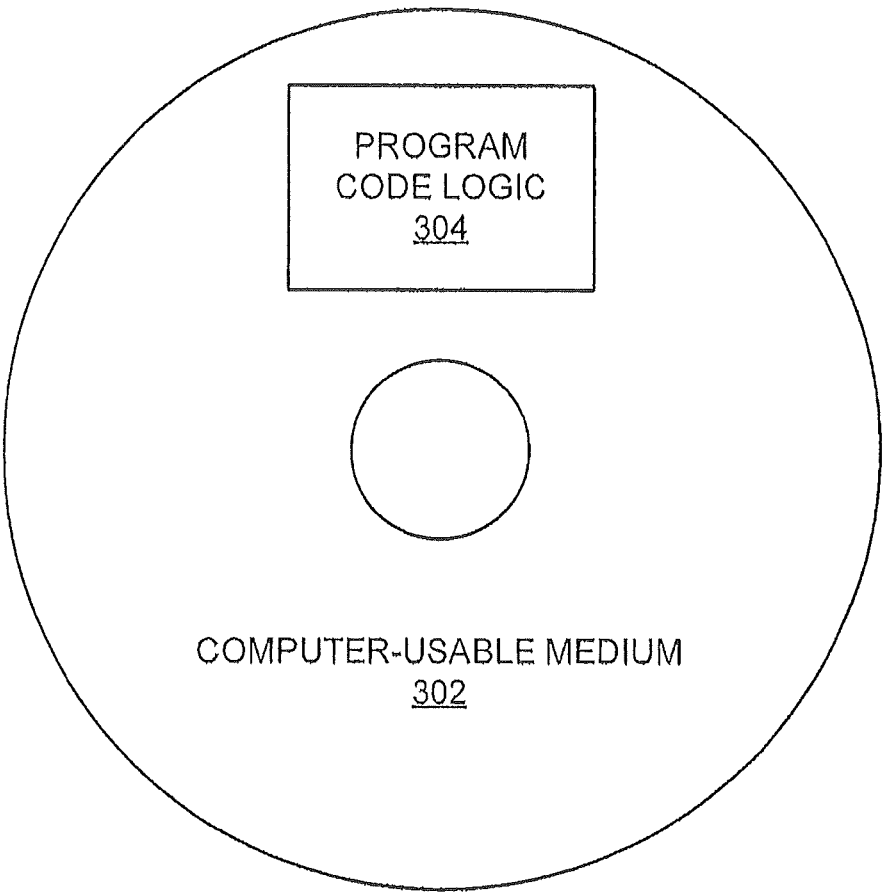
FIG. 9 is an exemplary computer-usable medium in accordance with exemplary embodiments described herein.

Therefore, embodiments can be embodied in the form of computer-implemented processes and apparatuses for practicing those processes on a computer program product. Embodiments include the computer program product 300 as depicted in FIG. 9 on a computer usable medium 302 with computer program code logic 304 containing instructions embodied in tangible media as an article of manufacture. Exemplary articles of manufacture for computer usable medium 302 may include CD-ROMs, hard drives, universal serial bus (USB) flash drives, or any other computer-readable storage medium, wherein, when the computer program code logic 304 is loaded into and executed by a computer, the computer becomes an apparatus for practicing the invention. Embodiments include computer program code logic 304, for example, whether stored in a storage medium, loaded into and/or executed by a computer, or transmitted over some transmission medium, such as over electrical wiring or cabling, through fiber optics, or via electromagnetic radiation, wherein, when the computer program code logic 304 is loaded into and executed by a computer, the computer becomes an apparatus for practicing the invention. When implemented on a general-purpose microprocessor, the computer program code logic 304 segments configure the microprocessor to create specific logic circuits.

Any combination of one or more computer readable medium(s) may be utilized. The computer readable medium may be a computer readable signal medium or a computer readable storage medium. A computer readable storage medium may be, for example, but not limited to, an electronic, magnetic, optical, electromagnetic, infrared, or semiconductor system, apparatus, or device, or any suitable combination of the foregoing. More specific examples (a non-exhaustive list) of the computer readable storage medium would include the following: an electrical connection having one or more wires, a portable computer diskette, a hard disk, a random access memory (RAM), a read-only memory (ROM), an erasable programmable read-only memory (EPROM or Flash memory), an optical fiber, a portable compact disc read-only memory (CD-ROM), an optical storage device, a magnetic storage device, or any suitable combination of the foregoing. In the context of this document, a computer readable storage medium may be any tangible medium that can contain, or store a program for use by or in connection with an instruction execution system, apparatus, or device.

A computer readable signal medium may include a propagated data signal with computer readable program code embodied therein, for example, in baseband or as part of a carrier wave. Such a propagated signal may take any of a variety of forms, including, but not limited to, electromagnetic, optical, or any suitable combination thereof A computer readable signal medium may be any computer readable medium that is not a computer readable storage medium and that can communicate, propagate, or transport a program for use by or in connection with an instruction execution system, apparatus, or device.

Program code embodied on a computer readable medium may be transmitted using any appropriate medium, including but not limited to wireless, wireline, optical fiber cable, RF, etc., or any suitable combination of the foregoing.

Computer program code for carrying out operations for aspects of the present invention may be written in any combination of one or more programming languages, including an object oriented programming language such as Java, Smalltalk, C++ or the like and conventional procedural programming languages, such as the "C" programming language or similar programming languages. The program code may execute entirely on the viewer's computer, partly on the viewer's computer, as a stand-alone software package, e.g., from a networked system, partly on the viewer's computer and partly on a remote computer or entirely on the remote computer or server. In the latter scenario, the remote computer may be connected to the viewer's computer through any type of network, including a local area network (LAN) or a wide area network (WAN), or the connection may be made to an external computer (for example, through the Internet using an Internet Service Provider).

As described above, features of example embodiments include and other unique features not found in the art.

The methods and apparatus described herein are useful to deposit a multilayer film onto a substrate core, such as a core nanoparticle or a core microparticle. Core sizes on the order of 5 nanometers (nm) to 50 micrometers (µm) in diameter are particularly useful. Cores can be made from many materials provided that have controllable size distribution and have sufficient surface charge (either positive or negative) to bind polyelectrolytes. Exemplary cores composed of inorganic materials include $CaCO_3$ microparticles, $CaCO_3$ nanoparticles, other inorganic salts such as $MgCO_3$, calcium phosphate, silica particles, and iron oxide particles. Examples of core particles made from organic polymers include nanoparticles and microparticles made from polylactic acid (PLA), polylactic acid glycolic acid copolymer (PLGA), polyethylene glycol (PEG), chitosan, latex, hyaluronic acid, and gelatin. Additionally, cores can be composed of both inorganic and organic materials, for example $CaCO_3$ microparticles coprecipitated with poly-L-glutamate, sodium salt.

The generality and relative simplicity of the LBL film process permits the deposition of many different types of polyelectrolyte onto many different types of surface. Polypeptide multilayer films are a subset of polyelectrolyte multilayer films, comprising at least one layer comprising a charged polypeptide, such as a designed polypeptide. A key advantage of polypeptide multilayer films over films made from other polymers is their biocompatibility. LBL films can also be used for encapsulation. Applications of polypeptide films and microcapsules include, for example, nano-reactors, biosensors, artificial cells, vaccines and drug delivery vehicles.

The term "polyelectrolyte" includes polycationic and polyanionic materials having a molecular weight of greater than 1,000 and at least 5 charges per molecule. Suitable polycationic materials include, for example, polypeptides and polyamines. Polypeptides include, for example, a polypeptide such as poly-L-lysine (PLL), poly-L-arginine, poly-L-ornithine, poly-D-lysine, and poly-DL-lysine.Polyamines include, for example, polyvinyl amine, poly(aminostyrene), poly(aminoacrylate), poly (N-methyl amino acrylate), poly (N-ethylaminoacrylate), poly(N,N-dimethyl aminoacrylate), poly(N,N-diethylaminoacrylate), poly(aminomethacrylate), poly(N-methyl amino-methacrylate), poly(N-ethyl aminomethacrylate), poly(N,N-dimethyl aminomethacrylate), poly(N,N-diethyl aminomethacrylate), poly(ethyleneimine), poly (diallyl dimethylammonium chloride), poly(N,N,N-trimethylaminoacrylate chloride), poly(methyacrylamidopropyltrimethyl ammonium chloride), chitosan and combinations comprising one or more of the foregoing polycationic materials. Suitable polyanionic materials include, for example, a polypeptide such as poly-L-glutamic acid (PGA),poly-L-aspartic acid, poly-D-aspartic acid, poly-L-gamma-glutamic acid, a nucleic acid such as DNA and RNA, alginate, carrageenan, furcellaran, pectin, xanthan, hyaluronic acid, heparin, heparan sulfate, chondroitin sulfate, dermatan sulfate, dextran sulfate, poly(meth)acrylic acid, oxidized cellulose, carboxymethyl cellulose, acidic polysaccharides, and croscarmelose, synthetic polymers and copolymers containing pendant carboxyl groups, and combinations comprising one or more of the foregoing polyanionic materials. In one embodiment, the RSV epitope and the polyelectrolyte have the same sign of charge.

A homopolymer is defined herein as a polymer made up of a single repeating monomeric subunit. For purposes of LBL fabrication, the monomeric subunit generally bears at least a single charge, either positive or negative. Thus for LBL purposes, the homopolymer usually is a polyelectrolyte. There are a wide variety of homopolymers useful in LBL. Of particular importance are polymeric amino acids such as poly-L-glutamate, poly-L-aspartate, poly-L-lysine, and poly-L-arginine, among others. When a homopolymer is composed of repeating amino acids it can also be referred to as a homopolypeptide. Herein the abbreviation used for homopolypeptide is HP.

In one embodiment, one or more polyelectrolyte layers of the film comprises a designed polypeptide (DP). Optionally, for convenience, designed polypeptides are chemically synthesized. In one embodiment, the design principles for polypeptides suitable for electrostatic layer by layer deposition are elucidated in U.S. Patent Publication No. 2005/0069950, incorporated herein by reference for its teaching of polypeptide multilayer films. Briefly, the primary design concerns are the length and charge of the polypeptide. Electrostatics is the most important design concern because it is the basis of electrostatic LBL. Without suitable charge properties, a polypeptide may not be substantially soluble in aqueous solution at pH 4 to 10 and cannot readily be used for the fabrication of a multilayer film by electrostatic LBL. Other design concerns include the physical structure of the polypeptides, the physical stability of the films formed from the polypeptides, and the biocompatibility and bioactivity of the films and the constituent polypeptides. In a specific aspect, the designed polypeptide comprises an epitope for a virus, bacteria, parasite or fungus and is suitable for eliciting an immune response.

A designed polypeptide means a polypeptide that has sufficient charge for stable binding to an oppositely charged surface, that is, a polypeptide that can be deposited into a layer of a multilayer film wherein the driving force for film formation is electrostatics. A short stable film is a film that once formed, retains more than half its components after incubation at in PBS at 37° C. for 24 hours. In specific embodiments, a designed polypeptide is at least 15 amino acids in length and the magnitude of the net charge per residue of the polypeptide is greater than or equal to 0.1, 0.2, 0.3, 0.4 or 0.5 at pH 7.0. Positively charged (basic) naturally occurring amino acids at pH 7.0 are arginine (Arg), histidine (His), ornithine (Orn), and lysine (Lys). Negatively charged (acidic) naturally occurring amino acid residues at pH 7.0 are glutamic acid (Glu) and aspartic acid (Asp). A mixture of amino acid residues of opposite charge can be employed so long as the overall net ratio of charge meets the specified criteria. In one embodiment, a designed polypeptide is not a homopolymer. In another embodiment, a designed polypeptide is unbranched.

In one embodiment, a designed polypeptide comprises a single antigenic epitope flanked by two surface adsorption regions, an N-terminal surface adsorption region and a C-terminal surface adsorption region. In another embodiment, a designed polypeptide comprises a single antigenic epitope flanked by one surface adsorption region linked to the N-terminus of the epitope. In another embodiment, a designed polypeptide comprises a single antigenic epitope flanked by one surface adsorption regions linked to the C-terminus of the epitope.

Each of the independent regions (e.g., epitopes and surface adsorption regions) of the designed polypeptide can be synthesized separately by solution phase peptide synthesis, solid phase peptide synthesis, or genetic engineering of a suitable host organism. Solution phase peptide synthesis is the method used for production of most of the approved peptide pharmaceuticals on the market today. A combination of solution phase and solid phase methods can be used to synthesize relatively long peptides and even small proteins. Peptide synthesis companies have the expertise and experience to synthesize difficult peptides on a fee-for-service basis. The syntheses are performed under good manufacturing practices (GMP) conditions and at a scale suitable for clinical trials and commercial drug launch.

Alternatively, the various independent regions can be synthesized together as a single polypeptide chain by solution-phase peptide synthesis, solid phase peptide synthesis or genetic engineering of a suitable host organism. The choice of approach in any particular case will be a matter of convenience or economics.

It should be emphasized that the above-described embodiments of the present invention, particularly, any detailed discussion of particular examples, are merely possible examples of implementations, and are set forth for a clear understanding of the principles of the invention. Many variations and modifications may be made to the above-described embodiment(s) of the invention without departing from the spirit and scope of the invention. All such modifications and variations are intended to be included herein within the scope of this disclosure and the present invention and protected by the following claims.

What is claimed is:

1. A system for automated synthesis of particles, the particles containing at least one polyelectrolyte layer deposited onto substrate cores, the system comprising:

a computer;

a tangential flow filtration (TFF) component comprising a TFF loop and a permeate valve, the permeate valve configured to selectively perform permeation steps via control by the computer, wherein the TFF loop comprises a particle reservoir holding a suspension of the substrate cores, a TFF filter, a connecting means that connects the particle reservoir and the TFF filter, and a product bag; wherein the tangential flow filtration loop comprises a closed-loop tubing network including the TFF filter, the particle reservoir, the connecting means, and the product bag; wherein the particle reservoir is in communication with a mechanical stirring means for maintaining dispersion of the substrate cores; and a soluble reagent addition manifold component, wherein the delivery of the soluble reagent from the soluble reagent delivery manifold component to the tangential flow filtration component is controlled by at least one valve controlled by the computer, wherein the soluble reagent comprises the polyelectrolyte, and wherein the closed loop tubing network extends to the soluble reagent addition manifold component and mounts to the at least one valve for the purpose of dispensing a reagent to the tangential flow filtration loop;

wherein the system provides a circulatory loop that provides a continuous flow path for synthesis of the particles containing at the least one polyelectrolyte layer deposited onto the substrate cores in an aseptic manner.

2. The system of claim 1, wherein the permeate valve and the at least one computer controlled valve of the soluble reagent addition manifold component are external to the continuous flow path.

3. The system of claim 1, wherein the permeate valve and the at least one computer controlled valve of the soluble reagent addition manifold component are fully automated under computer control and without user initiation.

4. The system of claim 1, the system being configured to enable:

automated delivery of a defined volume of the soluble reagent from the soluble reagent addition manifold component to the tangential flow filtration component;

mixing of the soluble reagent with the substrate core particles for a defined time in the TFF loop;

eliminating of excess soluble reagent by permeation for a defined volume in the TFF loop; and delivering a defined volume of a second regent having an opposite polarity to the polyelectrolyte in the soluble reagent via the soluble reagent manifold component.

5. The system of claim 1, wherein the soluble reagent delivery manifold component comprises plural computer controlled valves for delivery of plural reagents to the TFF component.

6. The system of claim 5, wherein the plural reagents include oppositely charged polyelectrolytes.

7. The system of claim 6, wherein the tangential flow filtration component and the soluble reagent delivery manifold component are configured to perform automatic layer by layer formation of multilayered films containing a plurality of oppositely charged polyelectrolyte layers, wherein at least one polyelectrolyte deposition cycle is at least partly automated by computer control of tangential flow filtration permeation steps and by computer control of delivery of plural reagents from the soluble reagent delivery manifold component.

8. The system of claim 7, wherein the substrate core has a diameter of 50 nm to 50 μm.

9. The system of claim 5, wherein the soluble reagent delivery manifold component enables controlled delivery by the computer of a washing buffer either to a waste component, to the tangential flow filtration component, or both.

10. The system of claim 1, wherein the soluble reagent delivery manifold component comprises at least one pump configured to propel the soluble reagent through a path containing one or more computer activated valves to the particle reservoir.

11. The system of claim 1, wherein the soluble reagent is delivered to the tangential flow filtration component from the reagent addition manifold component and well mixed so that a resulting polylelectrolyte concentration is predictable and reproducible.

12. The system of claim 11, wherein the polyelectrolyte concentration is within +/−20% of a desired polyelectrolyte concentration.

13. The system of claim 12, wherein the desired polyelectrolyte concentration is about 0.2 to 2.0 mg/mL.

14. The system of claim 1, wherein the soluble reagent delivery manifold component is configured to deliver at least one reagent to the TFF component, wherein the at least one reagent is propelled by one of a pumping means, gravity, syringe, or compressed gas.

15. The system of claim 1, wherein the tangential flow filtration component and/or the soluble reagent delivery manifold component additionally comprise at least one computer controlled vent.

16. The system of claim 1, wherein the soluble reagent delivery manifold component comprises a reagent metering device configured to indicate the volume or weight of delivered or undelivered soluble reagent.

17. The system of claim 16, wherein the metering device is configured to transmit data to the computer for the purpose of recording the times and amounts of delivered soluble reagent.

18. The system of claim 1, wherein the tangential flow filtration component comprises a volume metering device configured to report TFF circulatory loop volume data to the computer.

19. The system of claim 18, wherein the computer configured to maintain the loop volume of the mixture inside the tangential flow filtration component to within a set range by activation of valves to either increase the volume by addition of a reagent or decrease the volume by permeation.

20. The system of claim 1, wherein the computer includes a user interface configured to provide a user with computer prompts for user action.

21. The system of claim 20, wherein the prompts include indication of the need for a manual user click to initiate a polyelectrolyte deposition cycle.

22. The system of claim 1, wherein said computer includes a user interface configured to display the status of at least one polyelectrolyte deposition cycle.

23. The system of claim 1, wherein the tangential flow filtration component comprises a metering device to measure an amount of a permeate that passes through the filter during a particular polyelectrolyte deposition cycle step and reports that data back to the controlling computer.

24. The system of claim 23, wherein the computer automatically terminates a polyelectrolyte deposition cycle step upon measuring a user specified amount of permeate.

25. The system of claim 24, wherein the user specified amount of permeate is in the form of a signal from an electronic scale that continually measures the amount of permeate that exits the tangential flow filtration loop.

26. The system of claim 1, wherein the closed-loop tubing network is sterilized by treatment with gamma radiation, or ethylene oxide, or heat before mounting in the system.

27. The system of claim 1, wherein the closed-loop tubing network is configured to be mounted to a pump of the TFF component and the at least one computer controlled valve.

* * * * *